(12) United States Patent
Eaves, III

(10) Patent No.: US 10,094,401 B2
(45) Date of Patent: Oct. 9, 2018

(54) FIXATION DEVICE FOR SECURING A LINEAR ELEMENT TO A WORKPIECE

(71) Applicant: EMRGE, LLC, Atlanta, GA (US)

(72) Inventor: Felmont F. Eaves, III, Atlanta, GA (US)

(73) Assignee: EMRGE, LLC, Atlanta, GA (US)

( * ) Notice: Subject to any disclaimer, the term of this patent is extended or adjusted under 35 U.S.C. 154(b) by 498 days.

(21) Appl. No.: 14/706,572

(22) Filed: May 7, 2015

(65) Prior Publication Data
US 2015/0240852 A1 Aug. 27, 2015

Related U.S. Application Data

(63) Continuation of application No. PCT/US2013/069467, filed on Nov. 11, 2013.
(Continued)

(51) Int. Cl.
*A61B 17/04* (2006.01)
*F16B 5/00* (2006.01)
(Continued)

(52) U.S. Cl.
CPC ........ *F16B 5/0008* (2013.01); *A61B 17/0401* (2013.01); *A61B 17/0469* (2013.01);
(Continued)

(58) Field of Classification Search
CPC ............ A61B 17/0401; A61B 17/0487; A61B 2017/0404; A61B 2017/0414;
(Continued)

(56) References Cited

U.S. PATENT DOCUMENTS 2,075,508 A * 3/1937 Davidson ........... A61B 17/0401
24/712.9
3,664,345 A * 5/1972 Dabbs ................ A61B 17/0401
606/232
(Continued)

FOREIGN PATENT DOCUMENTS

CN 1151859 A 6/1997
CN 1217638 A 5/1999
(Continued)

OTHER PUBLICATIONS

European Extended Search Report in related EP Application No. 13854690.8, dated Jun. 6, 2016, 9 pages.
(Continued)

*Primary Examiner* — Josh Skroupa
(74) *Attorney, Agent, or Firm* — Additon, Higgins & Pendleton, P.A.

(57) ABSTRACT

A fixation device for securing a linear element to a workpiece includes a contact component and a fixation component. The contact component typically includes (i) a first contact surface for application to a workpiece and (ii) a first opening for receiving a linear element. The fixation component typically secures a portion of the linear element on a side of the first contact component opposite the first contact surface. The fixation component engages the contact component to prevent passage of the linear element's secured portion through the workpiece when a tension is applied to the linear element in a direction opposite the contact surface.

38 Claims, 20 Drawing Sheets

Related U.S. Application Data

(60) Provisional application No. 61/787,062, filed on Mar. 15, 2013, provisional application No. 61/727,373, filed on Nov. 16, 2012.

(51) Int. Cl.
  *F16B 5/06* (2006.01)
  *E04B 1/24* (2006.01)
  *A61B 90/00* (2016.01)

(52) U.S. Cl.
  CPC .. *A61B 17/0487* (2013.01); *A61B 2017/0404* (2013.01); *A61B 2017/0409* (2013.01); *A61B 2017/049* (2013.01); *A61B 2017/0411* (2013.01); *A61B 2017/0414* (2013.01); *A61B 2017/0438* (2013.01); *A61B 2017/0445* (2013.01); *A61B 2017/0453* (2013.01); *A61B 2017/0454* (2013.01); *A61B 2017/0456* (2013.01); *A61B 2017/0464* (2013.01); *A61B 2017/0488* (2013.01); *A61B 2090/037* (2016.02); *E04B 2001/2457* (2013.01); *F16B 2005/0678* (2013.01); *Y10T 403/471* (2015.01); *Y10T 403/472* (2015.01); *Y10T 403/7075* (2015.01); *Y10T 403/7123* (2015.01)

(58) Field of Classification Search
  CPC .... A61B 2017/0438; A61B 2017/0454; A61B 2017/0456; A61B 2017/0464; F16B 5/0008; F16B 11/006; F16B 2005/0678; Y10T 24/3969; Y10T 403/471; Y10T 403/472; Y10T 403/54; Y10T 403/71; Y10T 403/7123; E04B 2001/2457
  USPC ...... 403/266, 267, 291, 384, 388; 24/136 R; 52/223.11
  See application file for complete search history.

(56) References Cited

U.S. PATENT DOCUMENTS

| | | | |
|---|---|---|---|
| 3,976,079 A * | 8/1976 | Samuels | A61B 17/0466 24/115 M |
| 5,669,935 A | 9/1997 | Rosenman et al. | |
| 5,681,351 A | 10/1997 | Jamiolkowsi et al. | |
| 5,766,234 A | 6/1998 | Chen et al. | |
| 5,800,478 A | 9/1998 | Chen et al. | |
| 5,810,853 A | 9/1998 | Yoon | |
| 5,921,986 A * | 7/1999 | Bonutti | A61B 17/0401 606/215 |
| 6,409,743 B1 | 6/2002 | Fenton | |
| 7,033,380 B2 * | 4/2006 | Schwartz | A61B 17/0401 606/232 |
| 7,048,755 B2 * | 5/2006 | Bonutti | A61B 17/0487 24/122.3 |
| 7,670,361 B2 * | 3/2010 | Nesper | A61B 17/688 128/898 |
| 7,862,584 B2 * | 1/2011 | Lyons | A61B 17/0487 606/232 |
| 7,946,976 B2 * | 5/2011 | Gertner | A61F 5/0086 600/37 |
| 8,070,772 B2 * | 12/2011 | McGuckin, Jr. | A61B 17/0057 606/151 |
| 8,523,902 B2 * | 9/2013 | Heaven | A61B 17/0401 606/232 |
| 8,992,571 B2 * | 3/2015 | Milazzo | A61B 17/0487 606/232 |
| 9,078,644 B2 * | 7/2015 | Stone | A61B 17/0401 |
| 9,398,903 B2 * | 7/2016 | McClellan | A61B 17/0401 |
| 2005/0251160 A1 | 11/2005 | Saadat et al. | |
| 2010/0204731 A1 * | 8/2010 | Hart | A61B 17/0401 606/232 |
| 2011/0009895 A1 | 1/2011 | Gertner | |
| 2011/0098725 A1 | 4/2011 | Cox et al. | |
| 2011/0106155 A1 | 5/2011 | Theobald et al. | |
| 2011/0152927 A1 | 6/2011 | Deng et al. | |
| 2012/0065678 A1 | 3/2012 | James | |
| 2012/0150203 A1 | 6/2012 | Brady et al. | |
| 2012/0165865 A1 | 6/2012 | Fujisaki et al. | |
| 2013/0153029 A1 * | 6/2013 | Crume | H01L 31/02013 136/259 |

FOREIGN PATENT DOCUMENTS

| | | |
|---|---|---|
| EP | 0707829 A1 | 4/1996 |
| FR | 494960 A | 9/1919 |
| GB | 1319813 A | 6/1973 |
| JP | 48-11639 A | 4/1973 |
| JP | 48-59942 | 8/1973 |
| JP | 08-206123 A | 8/1996 |
| JP | 2001-508316 A | 6/2001 |
| WO | 01097676 A2 | 12/2001 |
| WO | 01097676 A3 | 12/2001 |
| WO | 2005086885 A2 | 9/2005 |
| WO | 2005086885 A3 | 9/2005 |
| WO | 2012135735 A2 | 3/2011 |
| WO | 2011126588 A1 | 10/2011 |
| WO | 2012/073944 A1 | 6/2012 |
| WO | 2013059600 A1 | 4/2013 |
| WO | 2014078237 A1 | 5/2014 |

OTHER PUBLICATIONS

Office Action in related Japanese Application No. 2015-542714 dated Jun. 29, 2017, 5 pages [FR 494960 previously cited.].
English-translation of Office Action in related Japanese Application No. 2015-542714 dated Jun. 29, 2017, 8 pages.
Office Action in related Chinese Application No. 2013380060183. X, dated Sep. 29, 2016, 10 pages.
International Search Report and Written Opinion, Application No. PCT/US2013/069467, dated Feb. 10, 2014, 12 pages.
Examination report No. 1 in related Australian Application No. 2013345041 dated Nov. 7, 2017, pp. 1-4.

\* cited by examiner

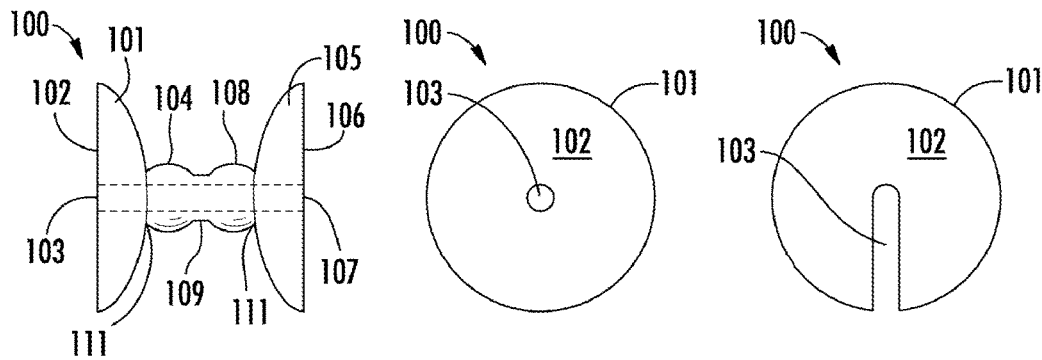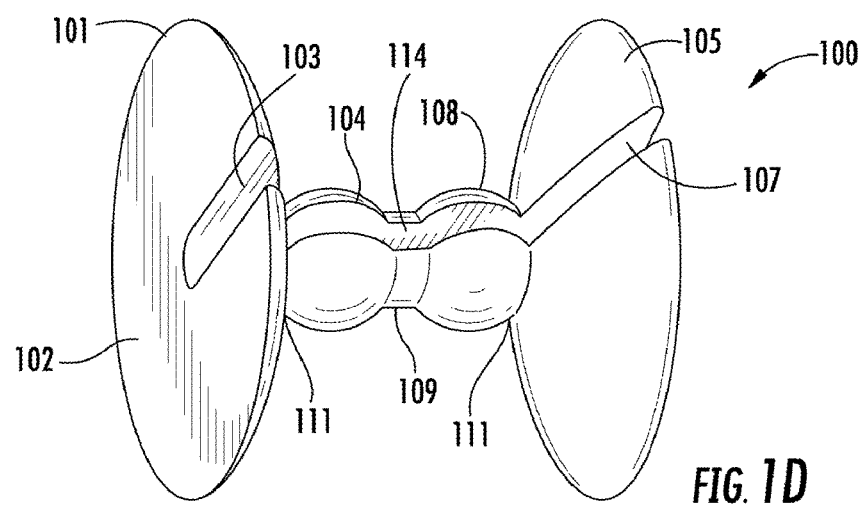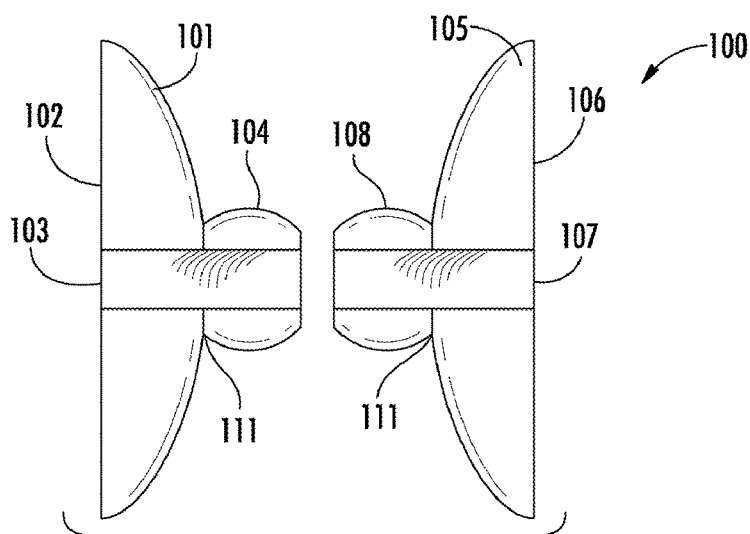

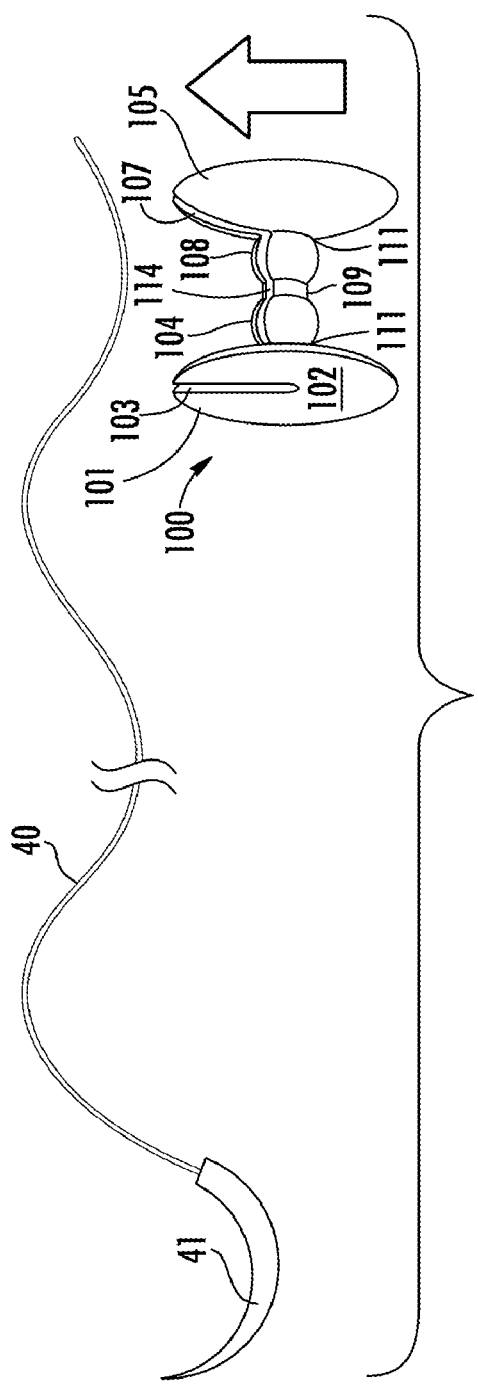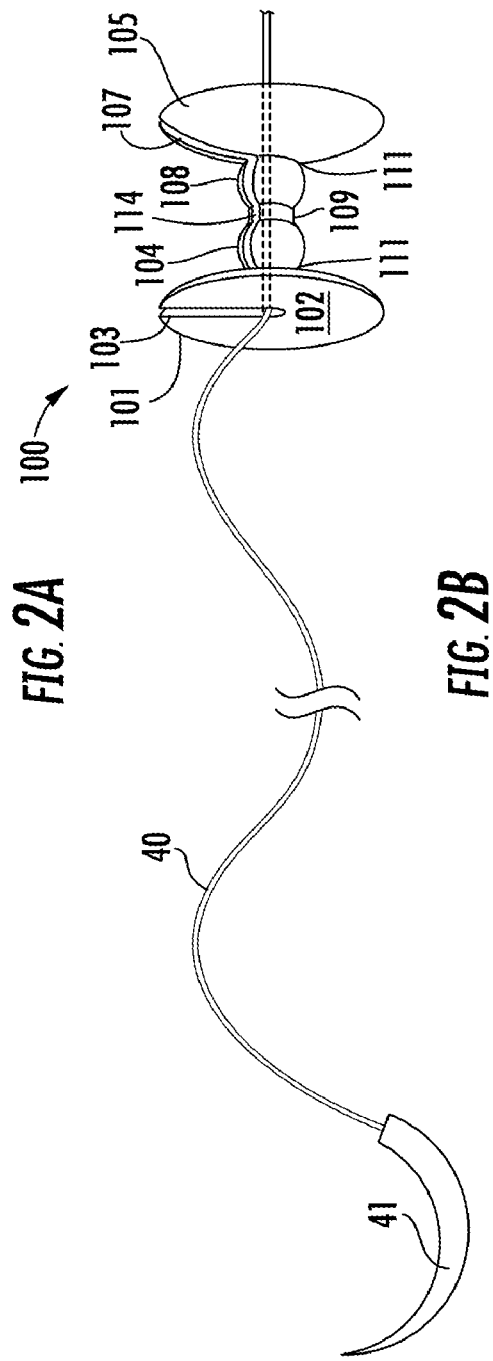
FIG. 2A
FIG. 2B

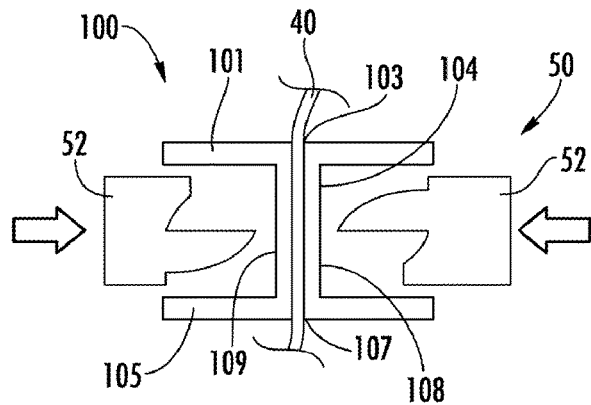
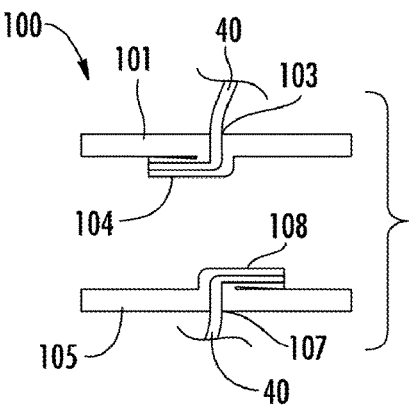
FIG. 4A   FIG. 4B
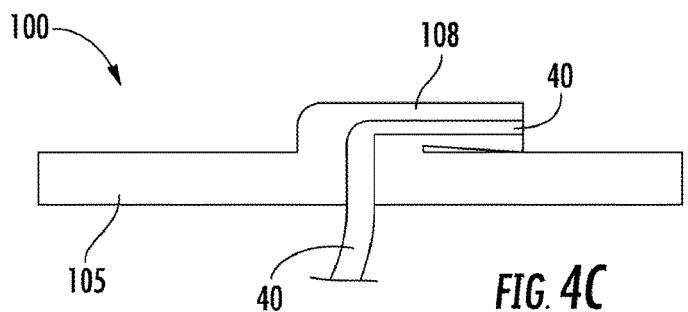
FIG. 4C
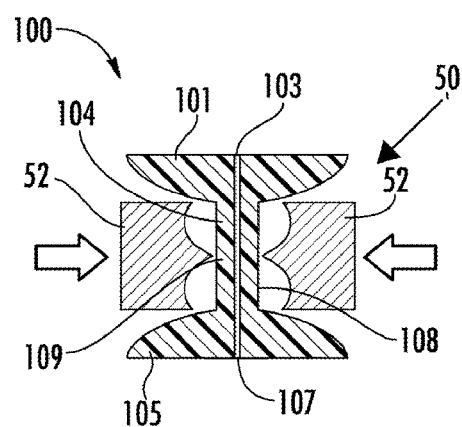
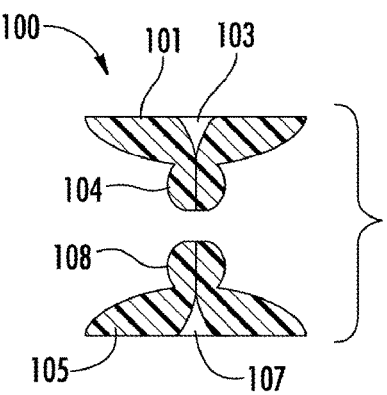
FIG. 4D   FIG. 4E

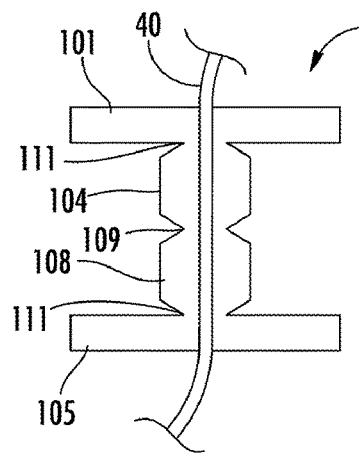
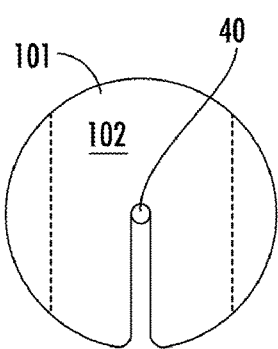
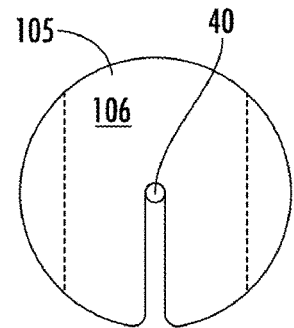
FIG. 16A
FIG. 16B
FIG. 16C
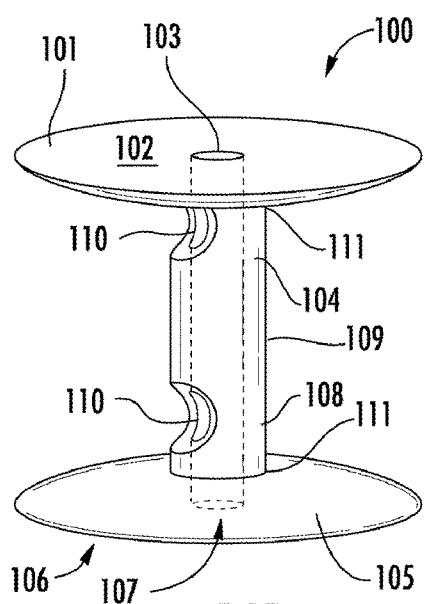
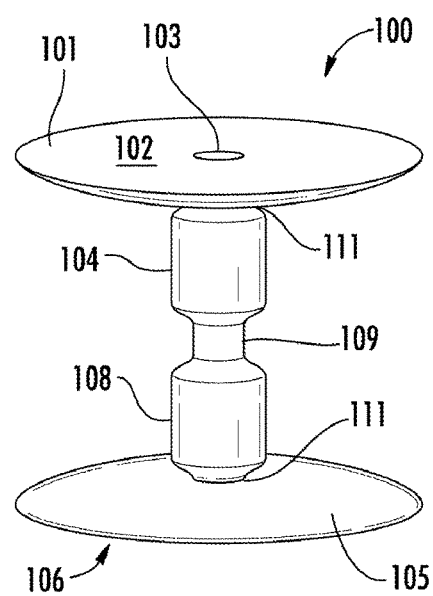
FIG. 16D
FIG. 16E

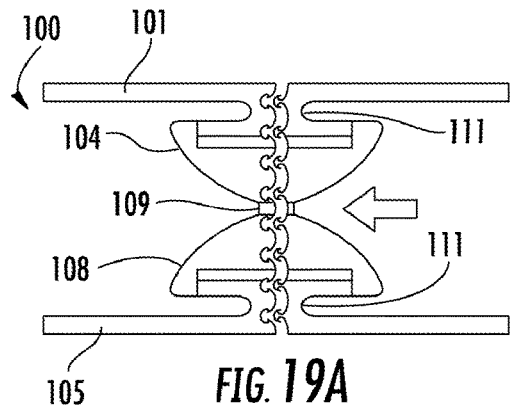
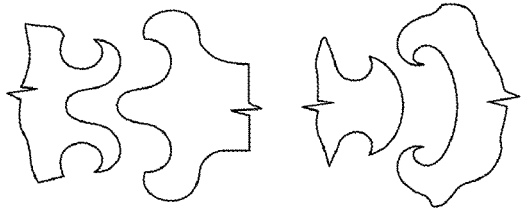
FIG. 19A   FIG. 19B   FIG. 19C
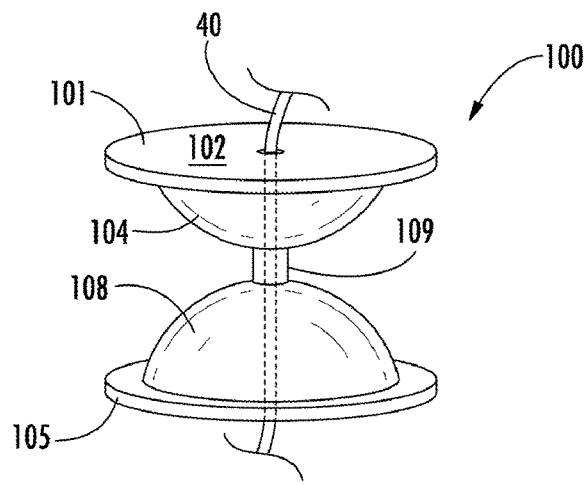
FIG. 19D
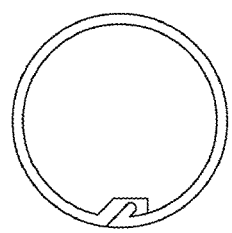 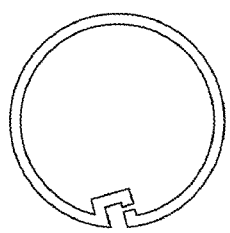
FIG. 19E   FIG. 19F

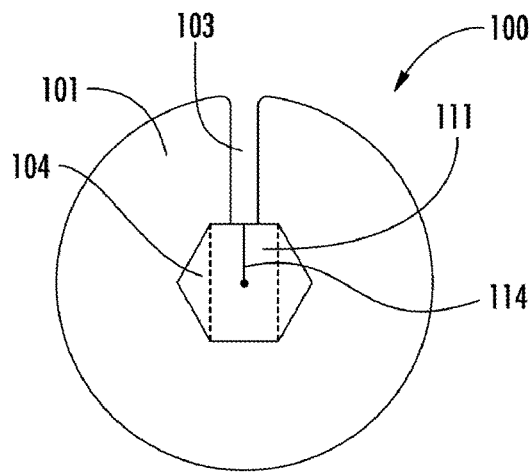
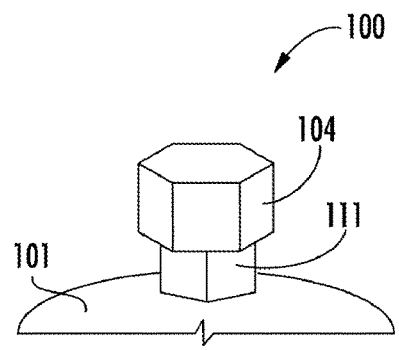
FIG. 23A  FIG. 23B
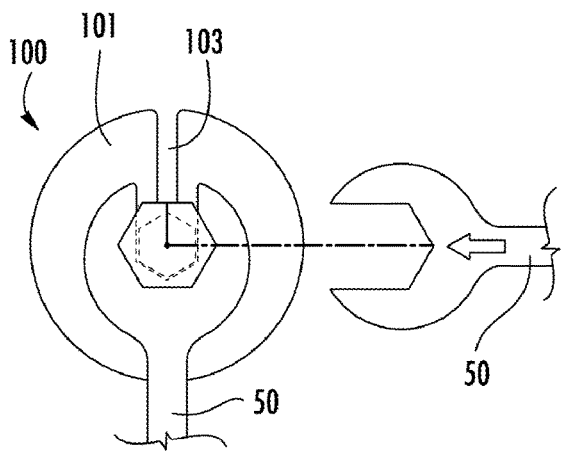
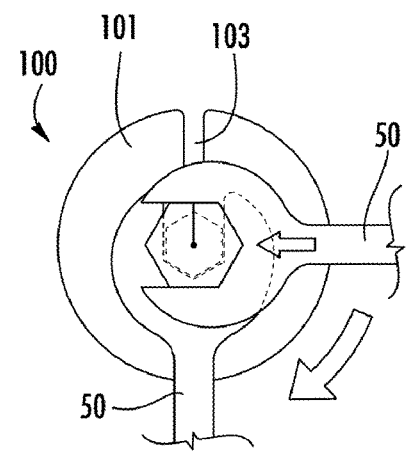
FIG. 23C  FIG. 23D

FIXATION DEVICE FOR SECURING A LINEAR ELEMENT TO A WORKPIECE

CROSS-REFERENCE TO PRIORITY APPLICATIONS

The present application claims the benefit of International Application No. PCT/US2013/069467 for a Fixation Device for Securing a Linear Element to a Workpiece filed Nov. 11, 2013 (and published May 22, 2014 as WIPO Publication No. WO 2014/078237), which claims the benefit of U.S. Patent Application No. 61/727,373 for a Fixation Device for Securing a Linear Element to a Workpiece (filed Nov. 16, 2012) and U.S. Patent Application No. 61/787,062 for a Fixation Device for Securing a Linear Element to a Workpiece (filed Mar. 15, 2013). Each of the foregoing patent applications and patent publication is incorporated herein by reference in its entirety.

BACKGROUND

Generally speaking, there is a need for fixation of linear elements that pass through a perforation in a work piece in many industrial, construction, and/or medical applications as well as other activities. Linear elements can include rigid structures (e.g., rods and/or dowels) and flexible (e.g., cord-like) structures (e.g., ropes, cables, sutures, wires, etc).

In some instances, the forces which act upon the linear element only act in a single direction. An example of such would be the suspension of a fixture or decorative element that travels through the ceiling with a clamping device on the upper surface of the ceiling. In this example, the weight of the fixture and connecting wire produce a downward force which is transferred to the clamping device which is subsequently pressed downward against the upper surface of the ceiling. In other words, the fixation device provides a single force vector resistance.

In other instances, such as in a metallic support rod in construction, the fixation needs to prevent the rod from moving toward or away from the workpiece (e.g., a beam). In other words, the fixation device provides a juxtaposed force vector resistance.

A device that is easily placed over a linear element and has strong fixation to the linear element can perform this task alone in the first instance (i.e., single force vector resistance), and when such a device is secured to the work piece can stabilize in the second instance (juxtaposed force vector resistance).

The placement of surgical sutures to close a skin wound provides a prototypical example of how a device that secures a linear element to a work piece may change the workflow and results compared to other methods of fixation. In traditional suture methods a needle with attached suture is passed sequentially through both sides of a wound, and then the "free" suture end (opposite the needle) is tied to a section of the suture strand between the needle and the free end to form a loop.

The problem with this method is that the tissues may not be ideally everted for optimal healing and the portion of the suture strand that lies over the surface of the skin can cause trauma and ultimately produce scars lying horizontal to the direction of the wound itself. In addition, removal of sutures can be uncomfortable as scissor tips need to be passed between the skin surface and the suture loop, placing additional tension on the sutures.

On the other hand, the placement of surgical sutures to the skin by means of surgical buttons eliminates the loop entirely and the possibility of horizontal scarring. If the free end of the suture (i.e., the end opposite the needle) is secured with a flat object (e.g., a surgical button, suture clip, or similar device) and the needle is passed through tissue, then the object is brought into contact with the skin on the object's flat surface as the suture is advanced, preventing the suture from passing all the way through the tissue and transferring any force on the suture to the skin. If a second button is secured to the suture on the opposite side of a wound, under appropriate tension, the wound is brought into contact and held there in a stable fashion. The suture strand may be cut and then reused. In traditional manifestations, surgical buttons and/or suture clips have been relatively cumbersome to use and, therefore, have not achieved widespread, common usage.

Therefore, a need exists for a fixation device that provides a flat surface for the transfer of tension in a linear element to a broad surface of the workpiece and facilitates simple and easy fixation and swift deployment.

SUMMARY

Accordingly, in one aspect, the present invention embraces a fixation device for securing a linear element to a workpiece that includes a first contact component and a first fixation component. The first contact component has a first contact surface for application to a workpiece and a first opening for receiving a linear element. The first fixation component secures a portion of the linear element on a side of the first contact component opposite the first contact surface. The first fixation component engages the first contact component to prevent passage of the linear element's secured portion through the workpiece when a tension is applied to the linear element in a direction opposite the first contact surface.

In an exemplary embodiment, the fixation device also includes a second contact component and a second fixation component. The second contact component has a second contact surface for application to a workpiece and a second opening for receiving a linear element. The second fixation component secures a portion of the linear element on a side of the second contact component opposite the second contact surface. The second fixation component engages the second contact component to prevent passage of the linear element's secured portion through the workpiece when a tension is applied to the linear element in a direction opposite the second contact surface. Typically, the first fixation component and the second fixation component are positioned between the first contact component and the second contact component.

In another exemplary embodiment, the first contact component and the first fixation component are physically connected.

In yet another exemplary embodiment, the second contact component and the second fixation component are physically connected.

In yet another exemplary embodiment, as measured in a plane parallel to the contact surface, the fixation device's cross sectional area at the area of engagement between the contact component and the fixation component is smaller than (i) the contact component's average cross sectional area and (ii) the fixation component's average cross sectional area.

In yet another exemplary embodiment, the exterior surface of the fixation device opposite the contact surface primarily includes smooth surfaces.

In yet another exemplary embodiment, the ratio of (i) the height of the fixation device as measured from the contact surface to the end of the fixation component opposite the contact surface to (ii) the maximum width of the contact surface is approximately one or less.

In yet another exemplary embodiment, the contact component's opening includes a hole.

In yet another exemplary embodiment, the contact component's opening includes a groove.

In yet another exemplary embodiment, the fixation component includes an adhesive.

In yet another exemplary embodiment, the fixation component includes a jagged surface for engaging the linear element.

In yet another exemplary embodiment, the fixation device is made of a material that is capable of being deformed using tools powered only by average human hand strength.

In yet another exemplary embodiment, the contact component's contact surface includes an adhesive, medication, and/or padding.

The foregoing illustrative summary, as well as other exemplary objectives and/or advantages of the invention, and the manner in which the same are accomplished, are further explained within the following detailed description and its accompanying drawings.

BRIEF DESCRIPTION OF THE DRAWINGS

FIGS. 1A-1D depict an exemplary embodiment of a bi-directional fixation device in accordance with the present invention.

FIG. 1E depicts another exemplary embodiment of a bi-directional fixation device in accordance with the present invention.

FIGS. 2A-2F depict an exemplary method of using another exemplary embodiment of a bi-directional fixation device and an exemplary applicator device in accordance with the present invention.

FIG. 4A depicts another exemplary method of using another exemplary embodiment of a bi-directional fixation device and another exemplary applicator device in accordance with the present invention.

FIG. 4B depicts the exemplary embodiment of a bi-directional fixation device of FIG. 4A.

FIG. 4C depicts a portion of the exemplary embodiment of a bi-directional fixation device of FIG. 4A.

FIGS. 4D-4E depict another exemplary method of using another exemplary embodiment of a bi-directional fixation device and another exemplary applicator device in accordance with the present invention.

FIG. 16A depicts another exemplary fixation device in accordance with the present invention.

FIGS. 16B and 16C depict another exemplary fixation device in accordance with the present invention.

FIG. 16D depicts another exemplary fixation device in accordance with the present invention.

FIG. 16E depicts another exemplary fixation device in accordance with the present invention.

FIG. 19A depicts another exemplary fixation device in accordance with the present invention.

FIGS. 19B and 19C depict close-up views of exemplary interlocking elements included in exemplary fixation devices in accordance with the present invention.

FIG. 19D depicts another exemplary fixation device in accordance with the present invention.

FIGS. 19E and 19F depict exemplary interlocking elements included in exemplary fixation devices in accordance with the present invention.

FIGS. 23A-23D depict another exemplary method of using another exemplary fixation device and another exemplary application device in accordance with the present invention.

DETAILED DESCRIPTION

Figure 2C:
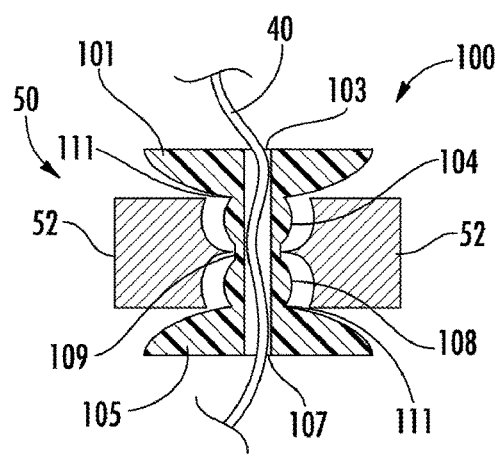

The present invention embraces a fixation device that provides a flat surface for the transfer of tension in a linear element to a broad surface of a workpiece and facilitates simple and easy fixation and swift deployment. In exemplary embodiments, the fixation device is formed of materials such as deformable polymers and supplementary adhesives. An exemplary fixation device is bi-directional and can be applied in either direction. In other words, the fixation device includes two halves that are mirror-images of each other.

In exemplary embodiments, the fixation device includes a fixation component that secures the linear element that is readily removed from the other component(s) of the fixation device. Typically, the fixation component can be removed without increasing the tension on the linear element. When the linear element is a suture, such embodiments facilitate the removal of the suture and reduce the pain experienced by the patient.

FIGS. 1A-1E depict exemplary embodiments of a bi-directional fixation device 100 in accordance with the present invention. The bi-directional fixation device is composed of two distinct fixation devices oriented in opposite directions along the longitudinal axis as defined by the most central point of the tunnel, channel, or groove exhibited (i.e., the first opening 103 and the second opening 107). As depicted, the left portion of the fixation device 100 includes a first contact component 101 having a first contact surface 102 for application to a workpiece and a first opening 103 for receiving a linear element. The left portion of the fixation device 100 also includes a first fixation component 104 for securing a portion of the linear element on the side of the first contact component 101 opposite the first contact surface 102.

The right portion of the fixation device 100 includes a second contact component 105 having a second contact surface 106 for application to a workpiece and a second opening 107 for receiving a linear element. The right portion of the fixation device 100 also includes a second fixation component 108 for securing a portion of the linear element on a side of the second contact component 105 opposite the second contact surface 106.

As depicted, the fixation device's left and right portions are physically connected at medial joint 109. Furthermore, the first contact component 101 and first fixation component 104 are physically connected. The second contact component 105 and the second fixation component 108 are also physically connected. That said, each of these portions and components may be physically separate from each other.

FIG. 1B depicts an exemplary embodiment of the fixation device 100 that a first opening 103 and a second opening 107 that form a closed tunnel, rather than the channel or groove depicted in FIGS. 1C and 1D.

As depicted, the composite device 100 has symmetrical individual fixation components, but other exemplary devices may include asymmetrical components. Furthermore the two component fixation devices can be physically separate or can be formed as a single composite unit. Upon activation which secures the linear element within each of the two component fixation devices, the component fixation devices can be separated and function independently. In this embodiment, each individual component fixation device demonstrates a lateral (or terminal) section (i.e., the first contact component 101 or the second contact component 105) that is typically wider than a central (or medial) section (e.g., the first fixation component 104 or second fixation component 108). The central (or medial) section is so designed that it can be activated to restrain a linear element within the groove, notch, channel, or tunnel to a degree that is required for usage. In some cases, the lateral section may also undergo a change in configuration or other change that assists in this function. Although either an individual (component) fixation device or a composite, bi-directional device may be formed of a single material, in other instances the central (medial) and lateral (terminal) sections can be composed of different materials.

FIGS. 2A-2F depict an exemplary method of using an exemplary embodiment of a bi-directional fixation device 100 in accordance with the present invention. FIGS. 2A-2B depict how a bi-directional fixation device 100 can first be applied to a linear element 40, herein demonstrating the example of a suture with a needle 41. The same principle can be applied to any linear element 40, either rigid or cord-like. The linear element 40 being fixed is positioned within the common channel, groove, or tunnel of the bi-directional fixation device 100 in a position along the longitudinal axis of the linear element 40.

Figure 2D:
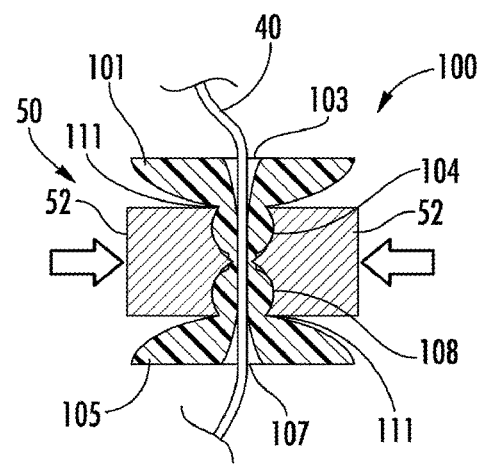
Figure 2E:
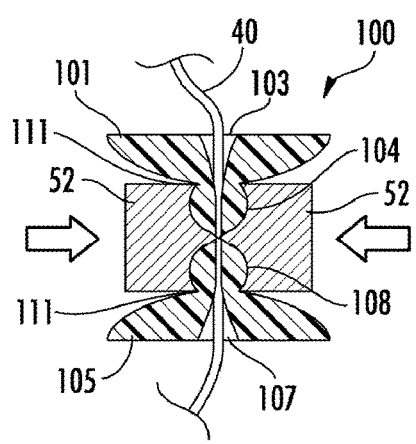
Figure 2F:
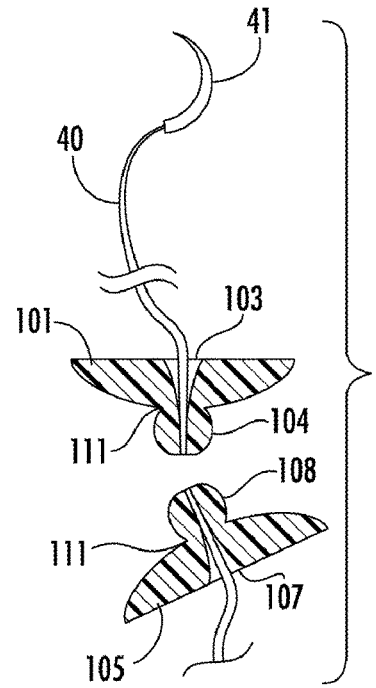

As depicted in FIGS. 2C-2D, the bidirectional device 100 is then activated so that the linear element 40 is firmly held by the fixation device 100. In this embodiment this fixation is by means of an applicator device 50 that deforms a malleable or deformable central section (e.g., the first fixation component 104, the second fixation component 108, and the medial joint 109), thus constricting the sides of the channel, groove, or tunnel of the central section against the contained linear element 40. (See FIG. 2D). The applicator device 50 thus functions as a crimper.

Furthermore, the applicator device 50 demonstrates specific features that enable this function, including surfaces to contract the body of the central (medial) section, a cutting element to divide the bi-directional fixation device 100 into the two component fixation devices after activation (See FIGS. 2E and 2F), and surface features to help hold, orient, or deploy the device 100. The applicator device 50 can be mechanically activated by manual pressure, pneumatic, electrical, or other means. In addition, the applicator device 50 may be designed to deploy either a single (component) fixation device, two physically separate (component) fixation devices so oriented as to function as a single bi-directional fixation device, and/or a bi-directional fixation device. In addition, the applicator device 50 may be of a single-load design, with new fixation devices loaded individually after each deployment, or may be a multi-load device, wherein new fixation devices are advanced into the deployment position by the applicator device 50. The applicator device 50 may be designed as an endoscopic instrument.

Figure 3A:
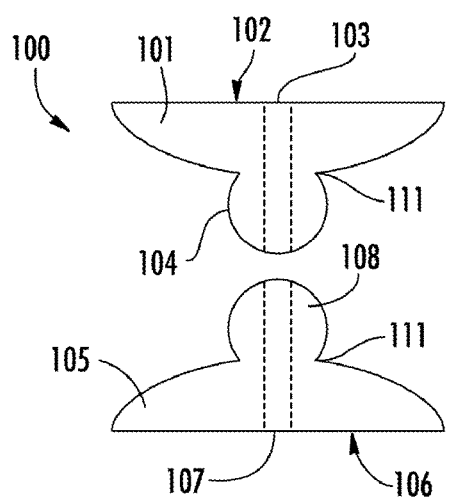
FIG. 3A depicts another exemplary embodiment of a bi-directional fixation device in accordance with the present invention.

FIGS. 3A-3F depicts multiple exemplary embodiments of a fixation device 100 in accordance with the present invention and features thereof. The fixation device can have numerous shapes, material compositions, colors, profiles, or other characteristics. The central (medial, apical) section (i.e., the first fixation component 104, the second fixation component 108, and/or the medial joint 109) may have a smooth and/or high profile (e.g., to provide greater channel area for fixation) as shown, for example, in FIGS. 3C-3E. The central section may also have a lower profile (e.g., as shown in FIG. 3A) creating a smooth contour both alone and in conjunction with the lateral (terminal, contact) sections (i.e., the first contact component 101 and second contact component 105).

Figure 3B:
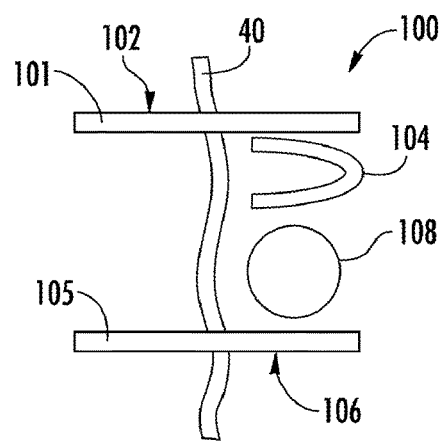
FIG. 3B depicts another exemplary embodiment of a bi-directional fixation device in accordance with the present invention.
Figure 3C:
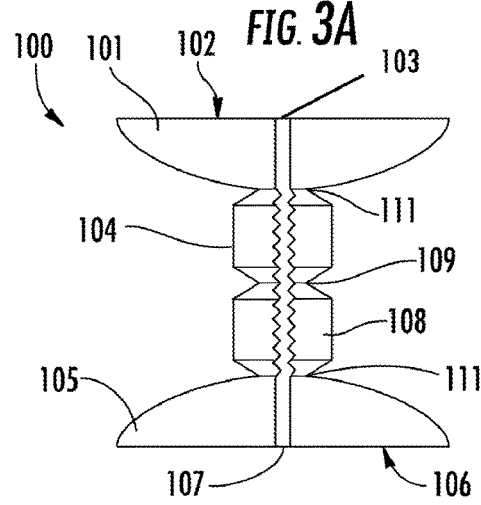
FIGS. 3C-3D depict another exemplary embodiment of a bi-directional fixation device in accordance with the present invention.
Figure 3D:
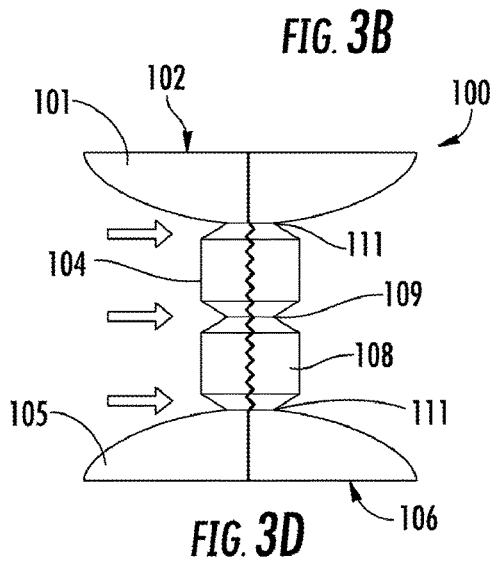

FIG. 3B depicts an exemplary embodiment of a fixation device 100 having lateral (terminal, contact) sections and medial (central, fixation) sections that are physically separate structures. The central section can assume the form of a clip as shown in the upper portion of FIG. 3B.

Figure 3E:
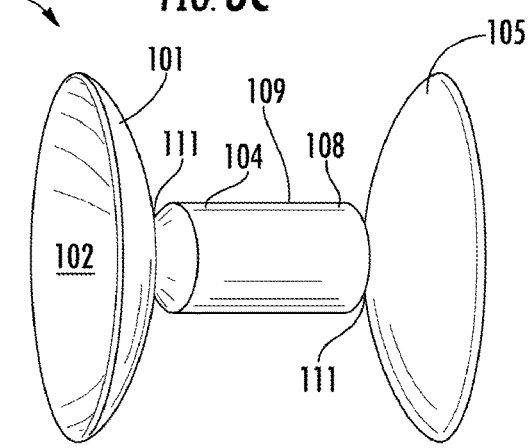
FIG. 3E depicts another exemplary embodiment of a bi-directional fixation device in accordance with the present invention.
Figure 3F:
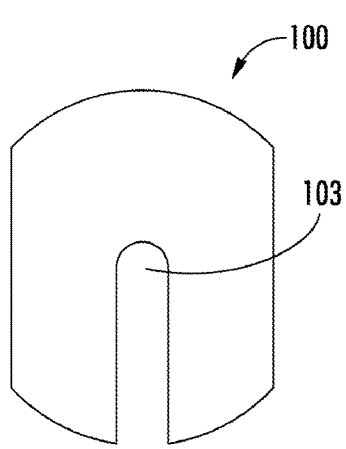
FIG. 3F depicts another exemplary embodiment of a bi-directional fixation device in accordance with the present invention.

The central sections can have a relatively straight configuration prior to deployment or can exhibit grooves, notches, flattened surfaces, holes, textures, bulges or other surface features to aid in positioning, alignment, securing, application, removal or function of the fixation device. Similarly, the lateral (terminal, contact) section may exhibit contour variations such as holes, notches, grooves, textures, flattened surfaces, or other surface features to aid in positioning, alignment, securing, application, removal, or function of the fixation device. For example, FIG. 3E depicts an exemplary fixation device 100 that includes a contact surface 102 having a cupped contour to improve the interface between the fixation device and a workpiece. FIG. 3F depicts an overhead view of an exemplary fixation component having flat sides to facilitate alignment of a fixation device 100 within an applicator device 50. Such features may interact with contours exhibited by applicator devices or may accommodate features of the surface to which the fixation device is in contact before, during, or after deployment.

FIGS. 4A-4C depict exemplary methods of using an exemplary embodiment of a fixation device 100 and an exemplary embodiment of an applicator device 50 in accordance with the present invention. As depicted, deformation of the central section (e.g., the first fixation component 104, the second fixation component 108, and the medial joint 109) occurs by a bending motion of the central section at approximately 90 degrees in relation to the longitudinal axis of a component (single) fixation device or bi-directional device. The bending also compresses the central section to constrict the tunnel, groove, or notch containing the linear element 40 and can position the deformed central section against the lateral (contact, terminal) section (i.e., the first contact component 101 or the second contact component 105) to reduce device height. See e.g., FIGS. 5C-5F. In addition, the lateral section in this embodiment can exhibit a groove, notch, or depression to accept the deformed central section. See e.g., FIGS. 5C-5F. The central section can be so constructed that a hole, window, or groove (i.e., access opening 110) is present at the transition zone where the bend angle is of greatest acuity, thus providing access to the contained linear element. See e.g., FIGS. 5C-5F. The access opening 110 allows the contained linear element 40 to be divided without separation of the central section from the lateral section. Other fixation means for facilitating fixation of the linear element 40 within the fixation device 100 may be employed, including heat application, integrated or applied adhesives (e.g., pressure sensitive adhesives, cyanoacrylates, etc.), light activation, mechanical activation (e.g., ultrasonic energy), pins, wedges, screws, posts, interlocking components or other means. The central section can be composed of material with inherent adhesive properties.

Figure 5A:
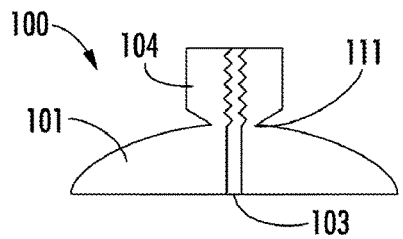
FIG. 5A depicts an exemplary fixation device in accordance with the present invention.
Figure 5B:
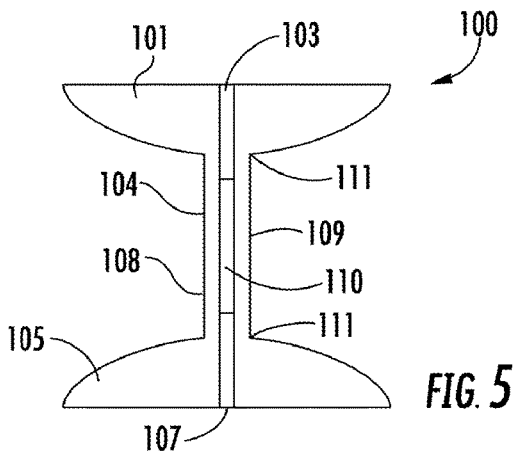
FIG. 5B depicts another exemplary embodiment of a bi-directional fixation device in accordance with the present invention.
Figure 5C:
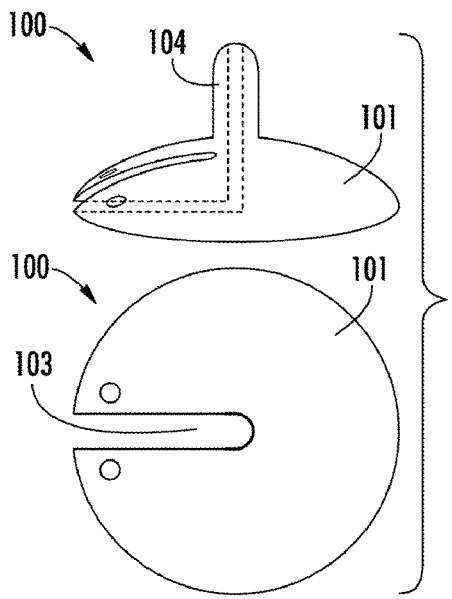
FIG. 5C depicts another exemplary fixation device in accordance with the present invention.
Figure 5D:
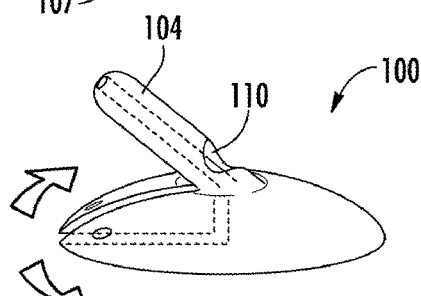
FIGS. 5D and 5E depict an exemplary method of using another exemplary fixation device in accordance with the present invention.
Figure 5E:
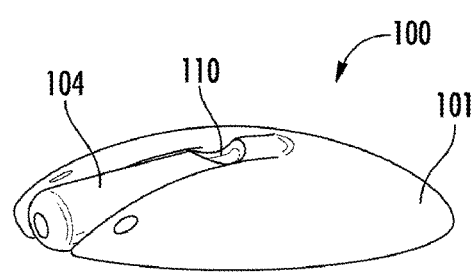
Figure 5F:
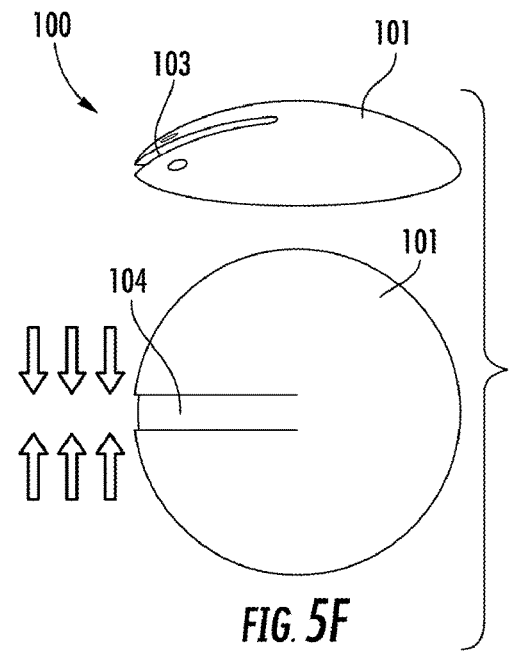
FIG. 5F depicts another exemplary method of using another exemplary fixation device in accordance with the present invention.
Figure 6:
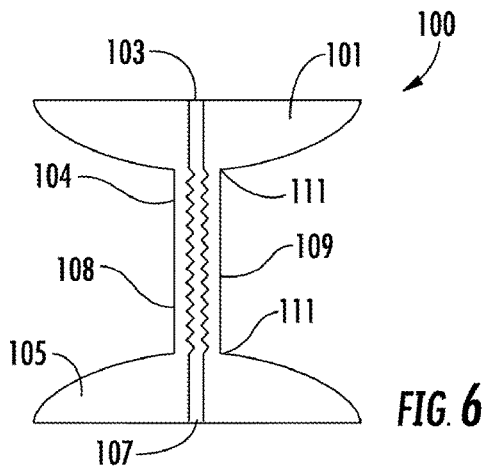
FIG. 6 depicts another exemplary embodiment of a bi-directional fixation device in accordance with the present invention.

FIGS. 5A-6 depict multiple exemplary embodiments of a fixation device 100 in accordance with the present invention and features thereof. As depicted in FIG. 5A, the central section (e.g., the first fixation component 104) and the lateral section (e.g., the first contact component 101) can be designed to connect at a transition zone 111 that is of a lesser width (in relationship to the longitudinal axis defined by the central channel, tunnel, or groove) than both the central and lateral sections. The transition zone 111 facilitates positioning and/or securing the fixation device 100 within an applicator, storage container, applicator-loading, or other device. The transition zone 111 can also facilitate separation of the central and lateral sections if such separation is desired, as in removal of the fixation device 100 from a workpiece.

As depicted in FIG. 6, the central channel, groove, or tunnel can exhibit striations, transverse grooves, textures, adhesives, waves, or other features to help secure the linear element 40 within the fixation device 100. These features may be confined to the lateral section, medial section, or to both sections.

The lateral section can be so configured to accommodate the central section during deployment as depicted in FIGS. 5D and 5E. In addition, the dimensions of the accommodating feature in the lateral section can be configured to have a lesser width than that of the central section, thereby providing a compressive force against the central section when the central section is positioned within the accommodating feature of the lateral section as depicted in FIG. 5F.

The contact surface of the lateral (terminal, contact) section (i.e., the first contact component or the second contact component), typically the surface opposite the central section, can exhibit adhesives, medicaments, padding, absorbent materials, or other features to enhance use. For example, having a silicone coating on the contact surface may improve the function of the fixation device when it is in contact with the skin or tissue when the linear element is a suture. The central (medial) section can similarly exhibit features such as slots, grooves, notches, and/or surface features, that may function to assist in securing, deploying, or removing the fixation device or that may be used as secondary fixation points (e.g., for securing additional structures to the fixation device).

Figure 7A:
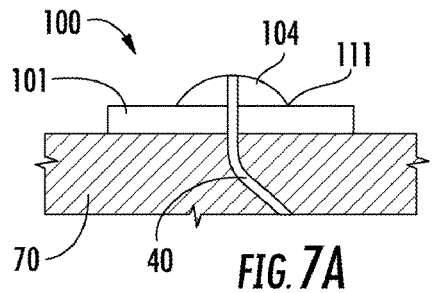
FIG. 7A depicts another exemplary fixation device in accordance with the present invention.
Figure 7B:
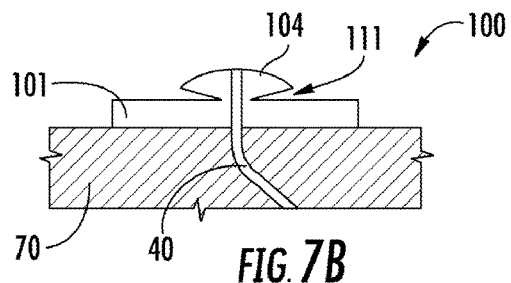
FIGS. 7B-7E depict another exemplary method of using another exemplary fixation device and an exemplary removal tool in accordance with the present invention.

FIGS. 7A-7E depict an exemplary method of using an exemplary embodiment of a fixation device 100 and an exemplary embodiment of a removal tool 60 in accordance with the present invention. FIG. 7A depicts a fixation device 100 that includes a flexible fixation component 104 that deforms to allow the removal tool 60 to slide between the fixation component 104 and the contact component 101. FIG. 7B depicts a fixation device 100 having a narrow transition zone 111 between the fixation component 104 and contact component 101 to allow the removal tool 60 to slide between the fixation component 104 and the contact component 101.

Figure 7C:
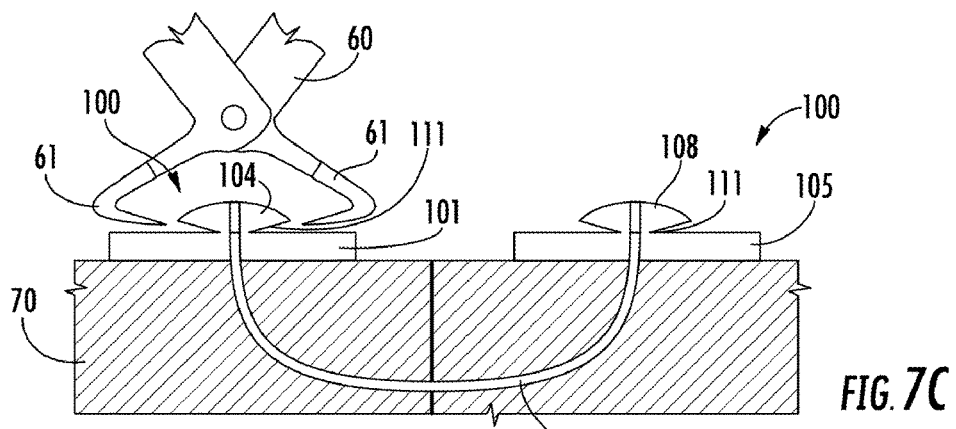
Figure 7D:
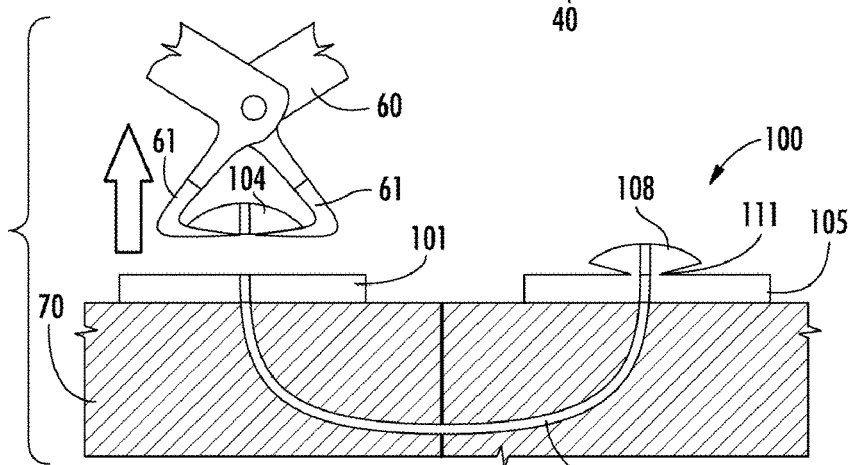
Figure 7E:
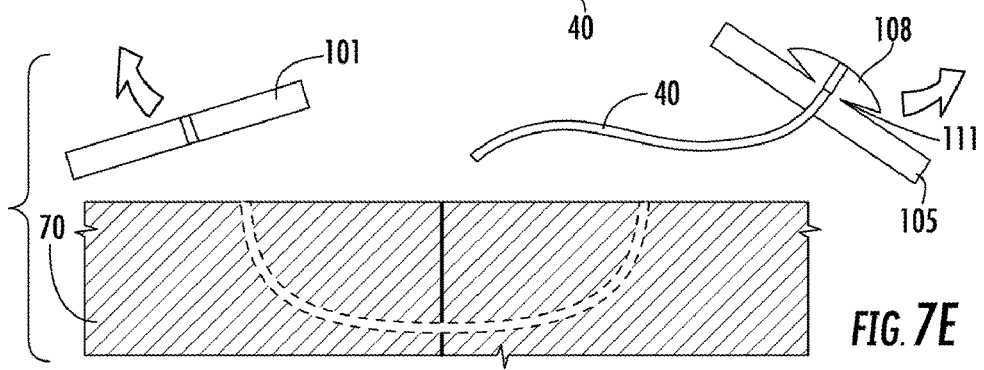

FIG. 7C depicts a linear element 40 secured to a workpiece 70 (e.g., a patient's skin) by two fixation devices 100 each having a contact component 101, a fixation component 102, and a narrow transition zone 111. A removal tool 60 is positioned over one of the fixation devices 100. In FIG. 7D, the removal tool has engaged and cut through the transition zone 111 and the linear element 40, thereby disconnecting the fixation component 102 from the contact component 101. Furthermore, the linear element 40 in FIG. 7D is only secured to the fixation device 100 on the right. FIG. 7E depicts the removal of the fixation device 100 on the right, along with the linear element 40, from the workpiece 70 and the removal of the contact component 101 from the workpiece 70.

Once deployed (i.e., secured to a workpiece), the fixation device 100 can be removed by a variety of methods, including release of the central (fixation) section, separation of the central section from the lateral (contact) section, unbending, untwisting, or unscrewing the central section from the lateral section, repositioning pins or other fixation structures, dividing the linear element at a point between the zone of linear element fixation and the contact surface of the lateral section, or dividing the linear element at a point between the contact surface of the lateral section and the surface with which it interfaces. The linear element can be released by removing the central section. The release removal of the central section can be partial or complete, depending on the number, size, and position of the attachments between the central section and the lateral section (i.e., the transition zone). For example, if the central section is in two or more physically separate sections and the removal force divides the attachment between one component of the central section and the lateral section, a portion(s) of the central section may remain intact as the linear element is released.

Removal of the central section from the lateral section can also include division of the linear element at a point between the central section and the lateral section (i.e., the transition zone), thus releasing the linear element concurrently with the central section.

In another exemplary embodiment, the central section or transition zone can include a hole, window, groove, or other feature that allows the linear element to be accessed and cut within the transition zone without removing the central section from the lateral section. The liner element could be cut using scissors, a knife, a scalpel, or a special cutting instrument specifically designed to efficiently interact and be positioned over the fixation device. Additionally, an embodiment of a device to separate the central section from the lateral section can include a chamber or space in which the divided central section is captured upon separation from the lateral section at the transition zone.

FIGS. 7A-7E also demonstrate an embodiment of the fixation device wherein the overall composite shape of the central section and the lateral section, as deployed, assumes a smooth, low profile contour. Such a contour would provide potential benefits to the fixation device, such as reducing the chance that external forces could act upon or displace the fixation device. As an example, if the fixation device was in the form of a surgical button used to secure a suture through the skin, such a low profile would reduce the chance that the device will be hit, rubbed, or impacted in such a way that it could temporarily displace the fixation device and thus cause a patient pain or cause harm to a healing wound.

In yet a further method of use, if the linear element is an absorbable surgical suture material, the natural process of suture breakdown, e.g., hydrolysis, will proceed without user intervention. At the point in time that the suture lacks sufficient tensile strength to maintain structural integrity, both fixation devices will be released and may fall out spontaneously, or may be potentially wiped off the tissue surface, obviating the need for any specific suture or fixation device removal.

FIGS. 8A-10 depict an exemplary method of using an exemplary embodiment of a fixation device 100 in accordance with the present invention. Using the bi-directional fixation device 100, a cycle is created where the deployment of the bi-directional fixation device simultaneously completes the second part of a first two part linear element function and "pre-loads" a single component fixation device, properly oriented, on the linear element, thus completing the first part of the second two part linear fixation function.

FIGS. 8A-10 depict the placement of surgical sutures for exemplary purposes, but the principles of the method and device function would apply to other bi-directional fixation devices with either rigid or cord-like linear elements. At the start of the cycle depicted in FIG. 8A, a component fixation device 100 including a contact component 101 and fixation component 104 is attached to the free end of the suture 40. The fixation device 100 is oriented such that the contact component's contact surface 102, i.e., the surface opposite the fixation component 104, is closer in proximity to the suture needle 41 than the central section (i.e., the fixation component 104). The needle 41 is passed through the tissues as would typically be done to approximate the wound margins. See FIGS. 8A-8C. As the needle 41 emerges from the tissue and the suture 40 (i.e., the linear element) is advanced, the contact surface of the lateral section (i.e., contact component 101) of the first fixation device 100 is brought in contact with the skin, and with additional tension on the suture the wound margins are brought into appropriate alignment. See FIG. 9A. While this tension and approximation are maintained, a bi-directional fixation device 100 is positioned such that the suture 40 emerging from the tissue on the side of the defect opposite the component fixation device that is already attached lies within the central channel, groove, or slot of the bi-directional fixation device 100. While this position of the suture 40 within the bi-directional fixation device 100 is maintained, the contact surface 102 of one component lateral section (i.e., contact component 101) of the bi-directional fixation device 100 is brought into position against the second surface of the tissue. See FIG. 9B.

An applicator, which may have been used to hold and align the bi-directional fixation device 100), is activated to secure the suture 40 within the first fixation component 105 and the second fixation component 108. The activation of the applicator also separates the first fixation component 105 from the second fixation component 108 and cuts the suture 40. See FIG. 10.

Figure 8A:
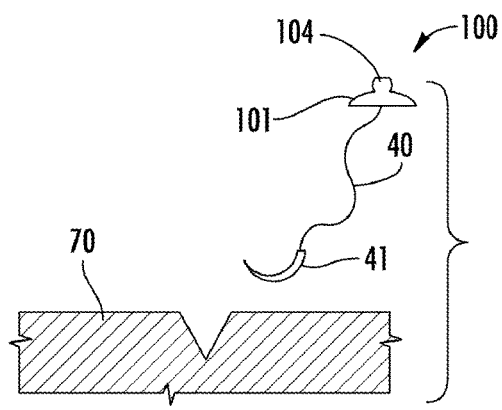
FIGS. 8A-8C, 9A, 9B, and 10 depict another exemplary method of using another exemplary fixation device in accordance with the present invention.
Figure 9A:
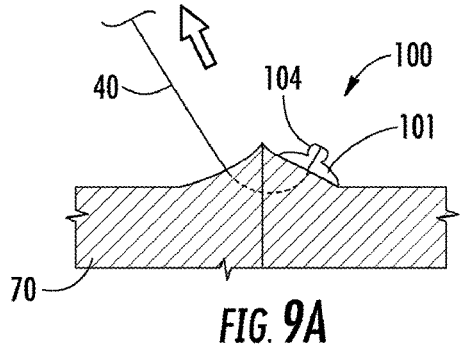
Figure 8B:
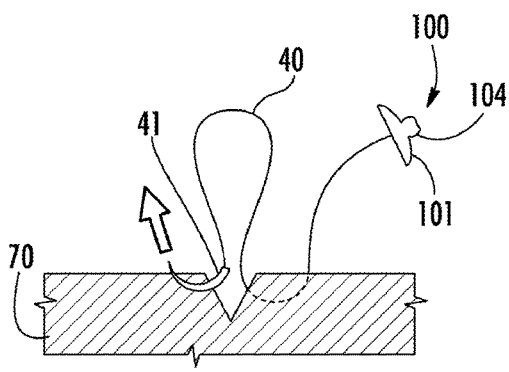
Figure 9B:
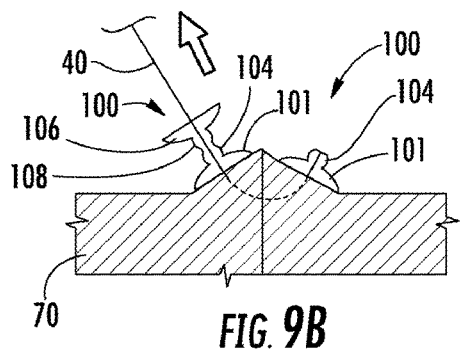
Figure 8C:
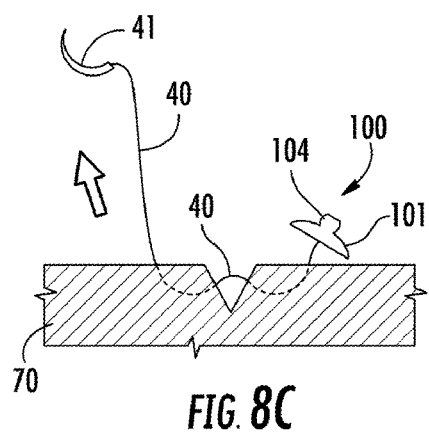
Figure 10:
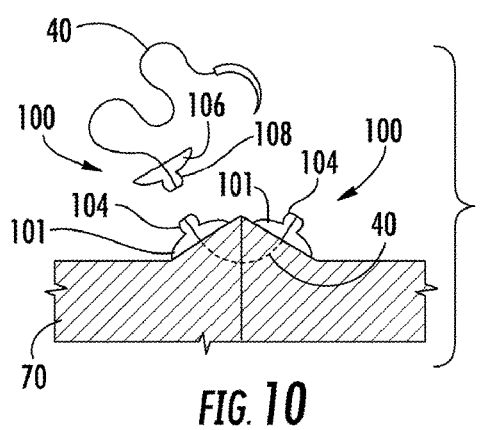

With the completion of deployment, the wound remains in proximity with both ends of the divided suture secured within component fixation devices on both sides of the wound, and a component fixation device is pre-loaded and appropriately oriented for initiation of the next cycle. In other words, the suture 40, needle 41, and second, detached half of the fixation device 100 depicted in FIG. 10 can be used to initiate another wound approximation as depicted in FIG. 8A.

Because deployment of the bi-directional fixation device simultaneously completes the second half of one two-part fixation function and the first half of a second two-part fixation function, the placement of fixation devices becomes quicker and more efficient. In addition, because the linear element is divided immediately adjacent to the apex of the central section, there is essentially no waste of linear element length, thereby allowing greater utilization of the linear element as a function of length. As an example, use of the fixation device as a surgical button maximizes the number of individual wound approximations that can be achieved with a single suture-needle combination.

Figure 11A:
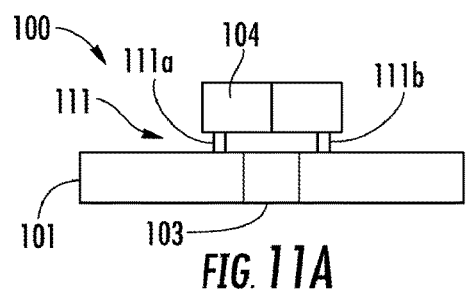
FIGS. 11A-11C depict another exemplary method of using another exemplary fixation device in accordance with the present invention.
Figure 11B:
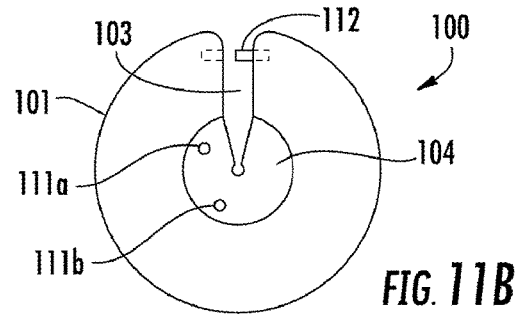
Figure 11C:
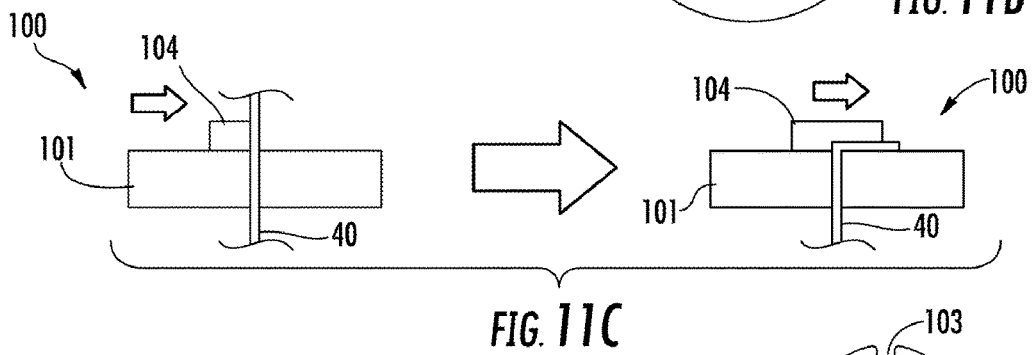

FIG. 11A depicts a side view of an exemplary fixation device 100, and FIG. 11B depicts an overhead view of the same exemplary fixation device 100. The fixation device 100 includes a contact component 101 having an opening 103 and a fixation component 104. The fixation device 100 also includes a transition zone 111 joining the contact component 101 and fixation component 104. The depicted transition zone 111 includes posts or rods connecting the contact component 101 and fixation component 104.

Exemplary embodiments of a fixation device in accordance with the present invention may include a central (medial) section connected to the lateral (contact, terminal) section by a transition zone that is elongated, septate, or discontinuous. For example, the transition zone can exhibit the form of posts or rods that connect the central section to the lateral section, potentially functioning both as a "spacer" to increase the distance between the lateral and central sections, but also facilitating function of the device.

FIG. 11B depicts transition zone connections 111a and 111b that are offset in relationship to the common channel, groove, of slot of the fixation device 100. The portion of the central section (i.e., the fixation component 104) which is attached to the lateral section (i.e., contact component 101) by the transition zone connections 111a and 111b remains stable during the application of a deforming, deployment force, while the portion of the fixation component 104 that is not attached to the contact component 101 is mobile in relationship to the common channel, groove, or slot.

The exemplary embodiment of FIG. 11B includes a contact component 101 having a post, pin, rod, or other surface feature (e.g., locking pin 112) that interfaces with a hole, slot, groove, or other surface feature on another portion of the contact component 101 such that the features interlock, connect, or secure the contact component 101 as they are approximated. By altering the attachments between the lateral section (i.e., contact component 101) and the central section (i.e., the fixation component 104), the central section can also rotate or pivot in relationship to the lateral section, thus securing a linear element to the fixation device.

FIGS. 12A-12D depict exemplary methods of using an exemplary fixation device 100 and an exemplary applicator device 50 in accordance with the present invention. Either a single component fixation device, two physically separate component fixation devices applied simultaneously, or a bi-directional fixation device can exhibit shape characteristics intended to interface with a specially designed deployment tool (e.g., an applicator device). Such surface features can include flat surfaces, slots, grooves, notches, bevels, or other forms and can be on the contact surface or body of the lateral section, the transition zone between the lateral section and the central section, within the body of the central section, or at the junction between two central sections in cases of a bi-directional device.

Figure 12A:
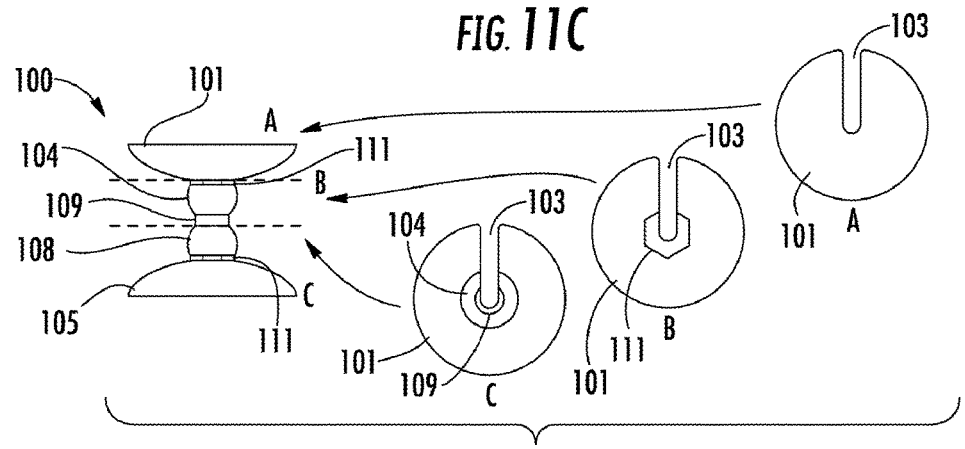
FIGS. 12A-12D depict another exemplary method of using another exemplary embodiment of a bi-directional fixation device and another exemplary applicator device in accordance with the present invention.
Figure 12B:
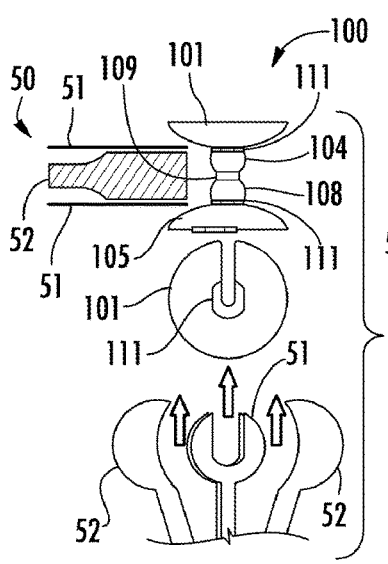
Figure 12C:
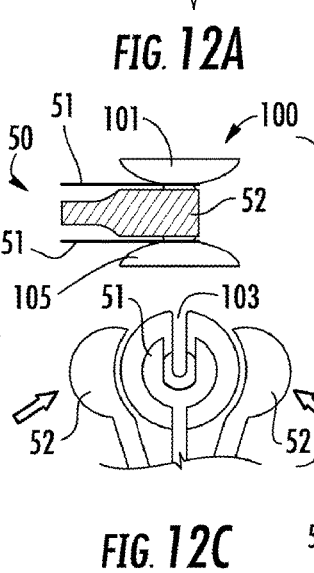
Figure 12D:
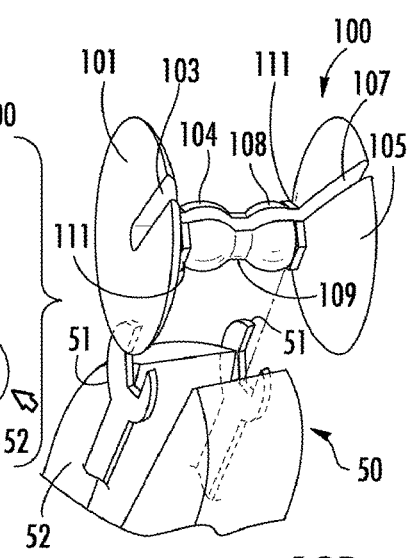

FIG. 12A-12D depict exemplary surface features. FIG. 12A includes cross-sectional views A, B, and C comparing the contact component's cross-section to the fixation device's cross-section in places A, B, and C shown on the left-side of FIG. 12A. As depicted in cross-section A, the contact component's cross-section is circular and interrupted by opening 103. As depicted in cross-section B, the transition zone 111 has a cross-section including flat surfaces parallel to the opening 103 for receiving an applicator device 50. See FIG. 12B. As depicted in cross-section C, the medial joint 109 has a circular cross-section that is smaller than the contact component's cross-section. Exemplary surface features include flattened surfaces on the transition zone between the central and lateral sections of a bi-direction fixation device.

An exemplary applicator device 50 includes applicator guides 51 which are essentially planar components that have a shape, as seen from above the plane, that has parallel flat edges of a size, shape, and orientation such that they can be advanced within the transition zone 111 and around the transition zone 111. In this exemplary embodiment, the applicator device 50 includes two such applicator guides, and as the applicator tool is advanced onto a bi-directional fixation device 100, each applicator guide interdigitates with the transition zone 111 of each component fixation device of the composite bi-directional fixation device 100. The applicator device 50 also exhibits two crimper arms 52 that are between the two applicator guides (See upper portions of FIGS. 12B and 12C) and move through a plane that is parallel to the two planes defined by the applicator guides 51.

As the applicator device 50 is advanced onto the bi-directional fixation device 100, the fixation device 100 is held into a consistent orientation in relationship to the applicator device 50, with the common groove, slot, or channel unhindered by the application device 50 such that it can be easily positioned in relation to a linear element. The crimper arms 52 (or other central section activating mechanism) are appropriately positioned and secured for deployment. As the crimper arms 52 are activated, the central section is deformed and the linear element is secured within the first fixation component 104 and the second fixation component 108. The crimper arms 52 can also include cutting elements that separate the two halves of the fixation device 100 and/or the linear element. In addition, the shape of the transition zone 111 and shape of either the applicator guides 51 or the crimper arms 52 may be designed such that the crimper arms 52 deform the central section when activated and the length of portions of the transition zone 111 are increased, thereby facilitating release of the applicator guides 51 from the transition zones 111.

Figure 13A:
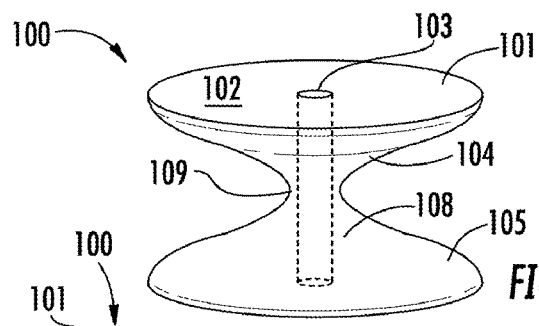
FIG. 13A depicts another exemplary fixation device in accordance with the present invention.
Figure 13B:
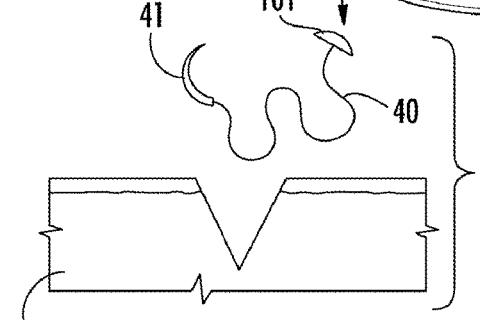
FIGS. 13B-13G depict another exemplary method of using another exemplary fixation device in accordance with the present invention.
Figure 13C:
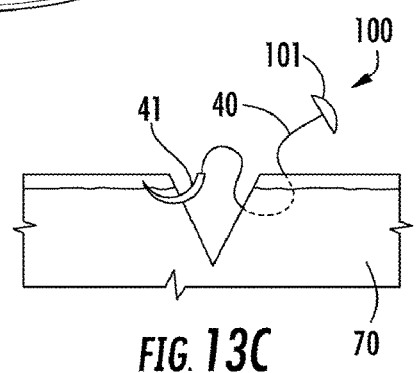
Figure 13D:
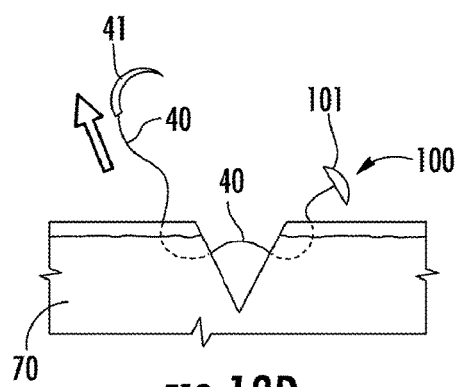
Figure 13E:
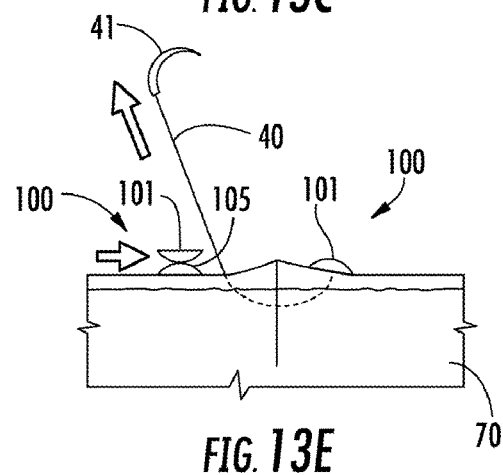
Figure 13F:
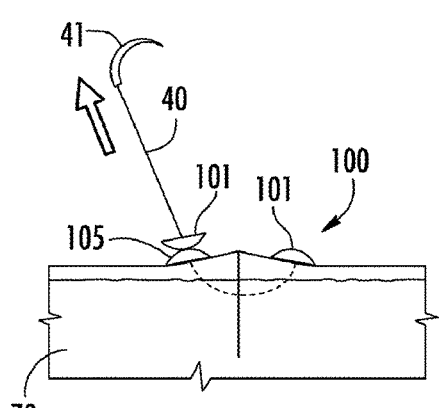
Figure 13G:
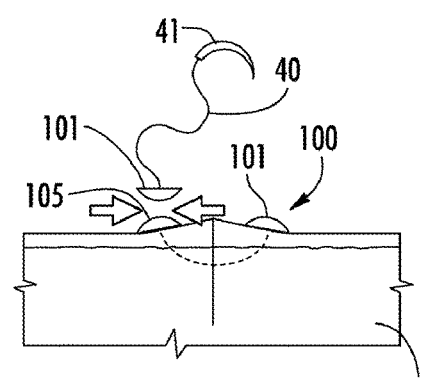

FIGS. 13A-13G depict an exemplary method of using an exemplary fixation device 100 in accordance with the present invention. As depicted in FIG. 13A, an exemplary bi-directional fixation device 100 can include a smooth transition between the contact and fixation components without a more narrow transition zone. As depicted, the fixation device receives a linear element 40 in a channel passing through the longitudinal length of the fixation device 100. FIGS. 13A-13G depict a method of using the fixation device 100 that is similar to that depicted in FIGS. 8A-10. The upper and lower portions of the fixation device 100 may be separated by deformation (e.g., using mechanical force), and/or heat. The linear element 40 may be secured within the fixation device 100 by such separation, adhesives, or by other mechanisms.

FIGS. 14A-14E depict an exemplary method of using an exemplary embodiment of a fixation device 100 and an exemplary embodiment of an applicator device 50 in accordance with the present invention. The transition zone 111 between the central and lateral sections (i.e., the fixation components 104 and 108 and the contact components 101 and 105) of a component fixation device or of a bi-directional fixation device can provide advantages during both application and removal of the fixation device 100. In this embodiment, the applicator device 50 includes crimper arms 52. The surfaces of the crimper arms 52 that contact the fixation device 100 include flat surfaces for compression and elevated features for division of the bi-directional fixation device 100 and the linear element 40 between the two fixation components 104 and 108. The engagement of the central sections (i.e., the two fixation components 104 and 108) with the compression surfaces of the applicator device 50 stabilize and secure the fixation device 100 and linear element 40, while the cutting surfaces of the applicator device 50 engage and cut through the medial joint 109.

Figure 14A:
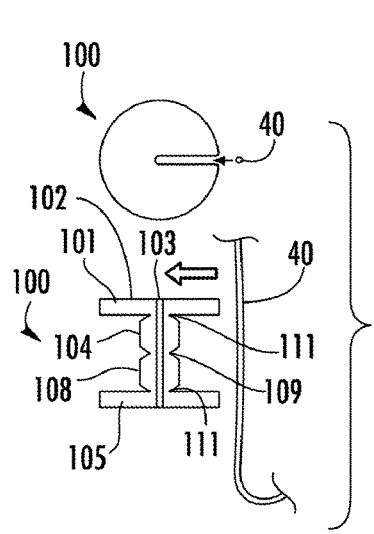
FIGS. 14A-14E depict another exemplary method of using another exemplary embodiment of a bi-directional fixation device and another exemplary applicator device in accordance with the present invention.

As depicted in FIG. 14A, the fixation device 100 includes a first contact component 101 having a first contact surface 102 and first opening 103 and a first fixation component 104. The fixation device 100 also includes a second contact component 105 having a second contact surface and second opening and a second fixation component 108. The first fixation component 104 and the second fixation component 108 are joined at medial joint 109 which is narrower than the fixation components. The fixation components 104 and 108 are joined to each respective contact component 101 or 105 by transition zones 111 that are narrower than the fixation components.

Figure 14B:
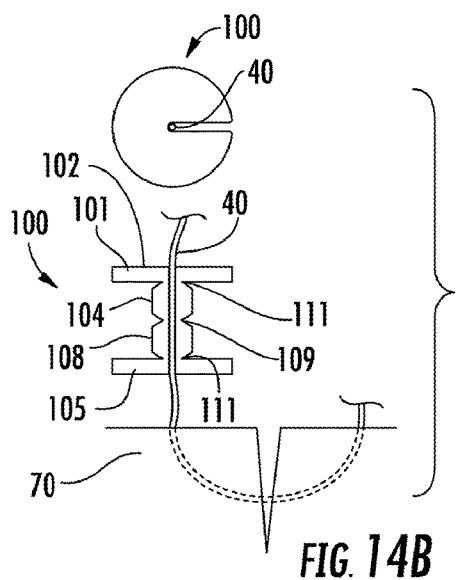
Figure 14C:
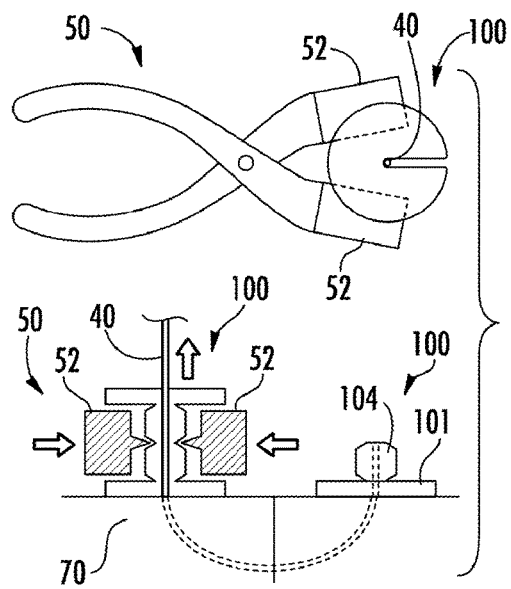
Figure 14D:
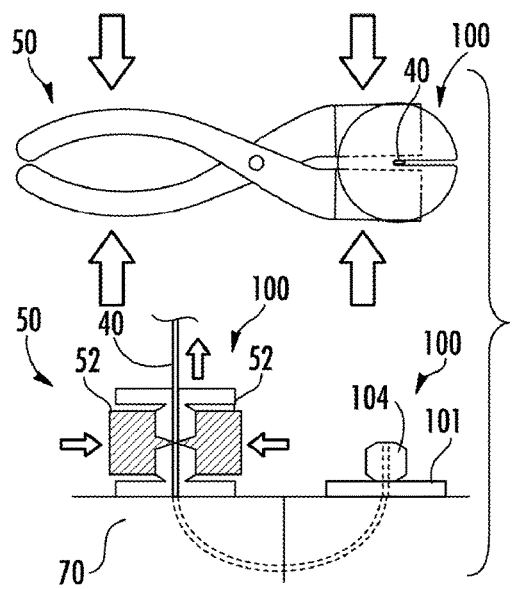
Figure 14E:
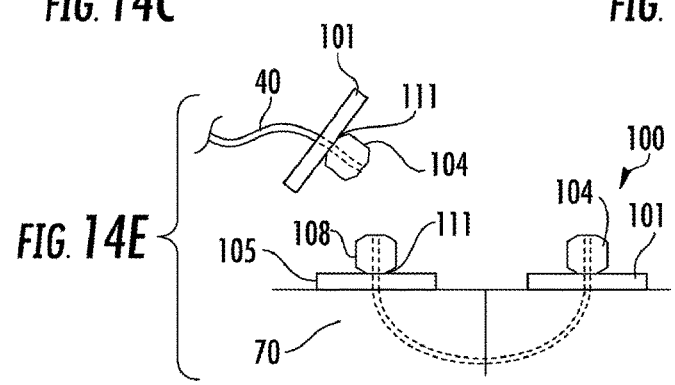
Figure 15A:
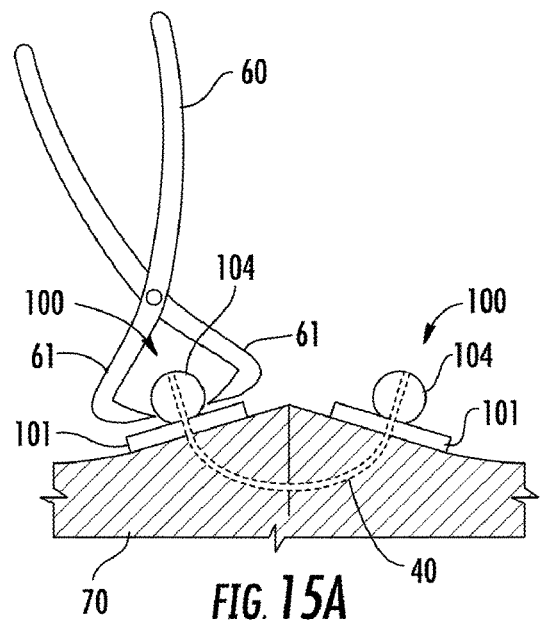
FIGS. 15A-15D depict another exemplary method of using another exemplary fixation device and an exemplary removal tool in accordance with the present invention.
Figure 15B:
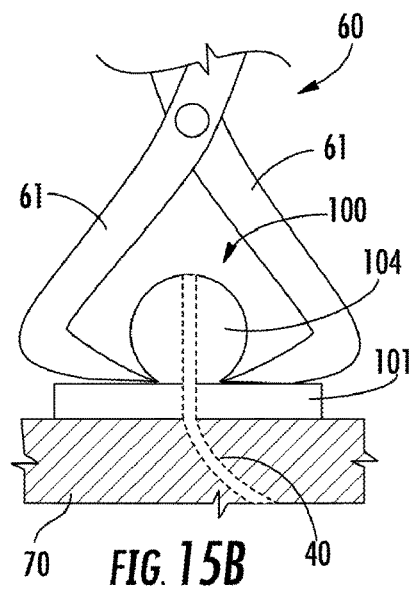
Figure 15C:
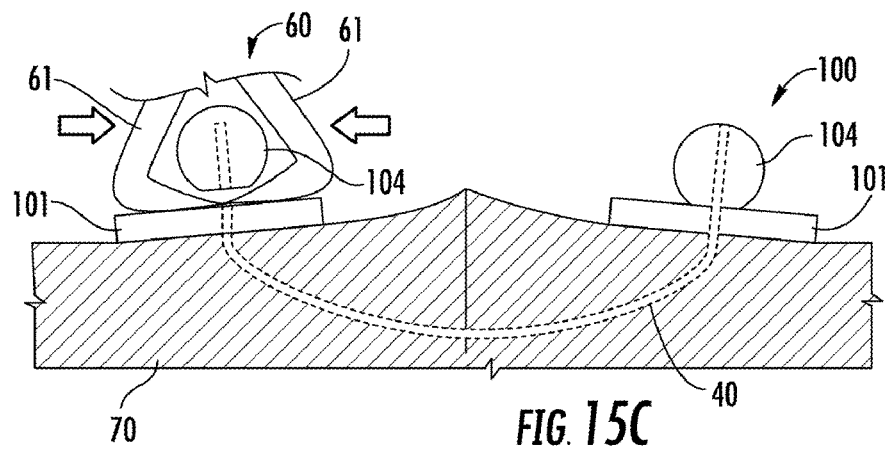
Figure 15D:
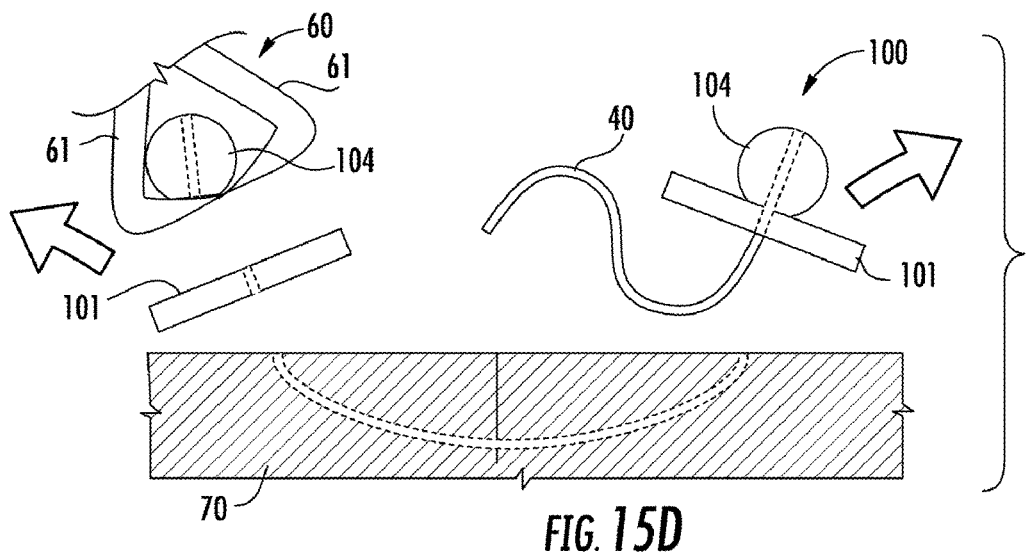

The linear element 40 may be placed in the fixation device's opening as depicted in FIG. 14A. An end of the linear element 40 may be passed through a workpiece 70 as depicted in FIG. 14B and secured by another fixation device 100 as depicted in FIG. 14C. The applicator device 50 is positioned over the fixation device 100 while tension is applied to the linear element 40 as depicted in FIG. 14C. The applicator device is further activated by compressive forces as depicted in FIG. 14D to compress the fixation components 104 and 108 around the linear element 40 and cut the medial joint 109 and linear element 40. FIG. 14E depicts the removal of the free section of the fixation device.

FIGS. 15A-15D depict exemplary methods of using an exemplary fixation device 100 and an exemplary removal tool 60 in accordance with the present invention. When fixation of a linear element 40 is limited to the central section (i.e., the fixation component 104), and the lateral section (i.e., the contact component 101) does not constrict or restrain the linear element 40, separation of the central section can assist in release of the linear element 40 from the fixation device 100. In exemplary embodiments where the central section remains intact after separation of the central and lateral sections, the linear element must typically also be divided. In embodiments where complete or partial separation of the central section from the lateral section releases the linear element (i.e., the central section does not remain in the deployed orientation), the released central section can be removed and linear element fixation released without division of the linear element.

Removal of a fixation device can be assisted by a removal tool. A removal tool can take multiple forms. FIGS. 15A-15D depict an exemplary removal tool 60 has two arms 61 that are brought into approximation, and the force of the approximation separates the central section from the lateral section. The space between the arms 61 could include a collection chamber such that the separated central section components are contained.

In another embodiment, the fixation device removal tool can be a rectangular box (not shown) with a hole near one end. The hole is typically of sufficient size and shape to accommodate the central sections of the fixation devices. The rectangular box typically also includes a movable blade parallel to the longitudinal axis of the removal tool configured such that the blade slides along a slot in the removal tool and closes the hole in the removal tool. In practice, such a removal tool would be positioned such that a central section of a fixation device lies within the hole of the removal tool, and that as the blade is advanced, the central section (and potentially the contained linear element) are separated from the lateral section, and the released central section is directed into the space within the box of the removal tool.

FIGS. 16A-16E depict exemplary embodiments of a fixation device 100 in accordance with the present invention. FIGS. 16B and 16C depict the contact surfaces 102 and 106 of two contact components 101 and 105 on either end of a bi-directional fixation device 100. As depicted by the dotted lines, the edges of the contact surfaces 102 may be removed to facilitate position of the fixation device 100.

FIG. 16D depicts a fixation device 100 that includes two access openings 110 in the fixation components 104 and 108. The access openings 110 provide access to a linear element within the fixation device's channel. When the fixation device 100 is secured to a workpiece, the linear element may be cut through the access opening 110 without increasing the tension on the linear element.

FIG. 16E depicts a fixation device 100 that includes transition zones 111 and a medial joint 109 that are narrower than the fixation components 104 and 108. These narrower portions of the fixation device 100 can facilitate positioning of the fixation device 100 and securing of a linear element by, for example, interacting with an applicator device or removal tool.

Many variations in configuration of the components, zones, and joints of the fixation device can be employed to improve the function of the fixation device. For example, the margins of the lateral section can assume the shape of a circle, can be configured with a slot or groove with beveled edges to assist in deployment or positioning, or can have a channel or groove which is offset, spiral, or asymmetric. Similar variations can be employed in the transition zone, central section, or connections between two central sections in bi-directional embodiments. The central sections and connecting sections can also be formed as tubes with perforations, grooves, or holes, or may exhibit a wave-like or zig-zag configuration to improve linear element fixation strength.

Figure 17A:
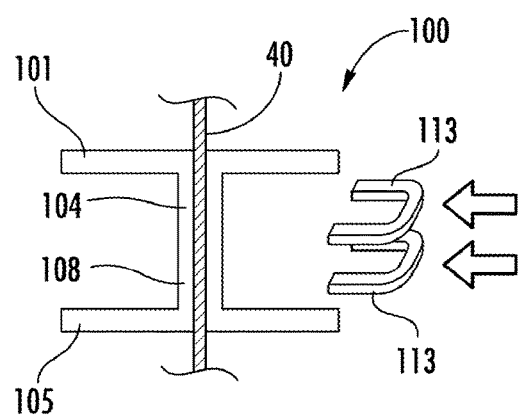
FIG. 17A depicts another exemplary fixation device in accordance with the present invention.

FIG. 17A depicts a fixation device including contact components 101 and 105 and fixation components 104 and 108. The fixation components 104 and 108 include clips 113 that are closed around the fixation components 104 and 108 and/or the linear element 40 between the contact components 101 and 105 to secure the linear element 40.

Figure 17B:
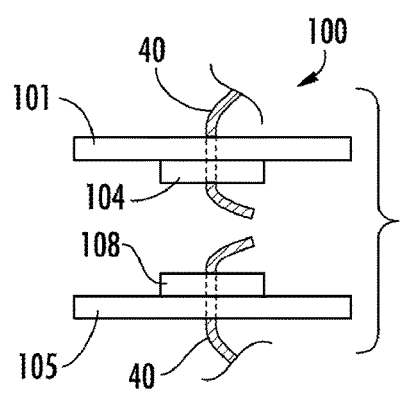
FIG. 17B depicts another exemplary fixation device in accordance with the present invention.

FIG. 17B depicts a fixation device including contact components 101 and 105 and fixation components 104 and 108 that are themselves clips. Thus, the fixation components 104 and 108 are not physically connected to the contact components 101 and 105. The fixation components 104 and 108 may also include tabs, folds, or other surface features that may be interfaced to assist in deployment or removal.

Off-set applicator tools such as that depicted in FIG. 4A can alter the mechanism of fixation device deployment by introducing a fold or bend in addition to compression of the central section. Fixation can be assisted by the presence of adhesives (e.g., pressure sensitive adhesives) incorporated into the central section or applied as a function of the applicator tool.

Figure 18A:
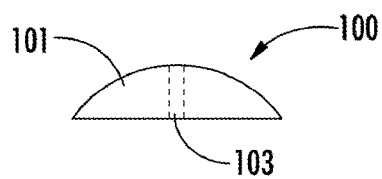
FIG. 18A depicts another exemplary fixation device in accordance with the present invention.

FIG. 18A depicts an exemplary fixation device 100 including a contact component 101 having an opening 103. A linear element is secured in the exemplary fixation device 100 by a fixation component that is not physically connected to the contact component 101.

Figure 18B:
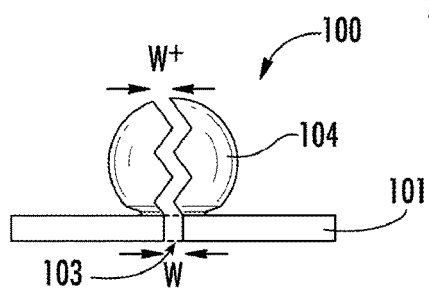
FIGS. 18B-18D depict another exemplary method of using another exemplary fixation device in accordance with the present invention.
Figure 18C:
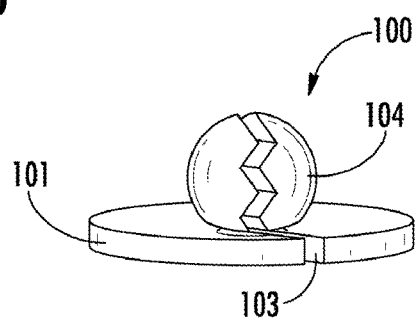
Figure 18D:
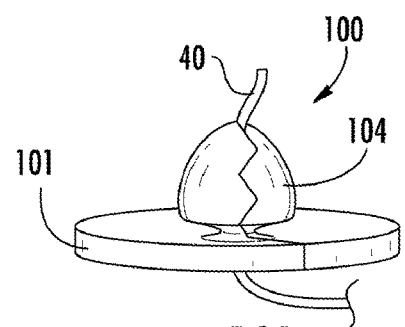

FIGS. 18B-18D depict an exemplary fixation device 100 that includes a contact component 101 and an interlocking fixation component 104. In a pre-loading state depicted in FIGS. 18B and 18C, the fixation component 104 includes an opening for receiving a linear element that is slightly narrower than the contact component's opening 103 (i.e., W is greater than $W^+$). A user places linear element 40 in the fixation device 100 and activates the fixation device (e.g., by pressing together the fixation device's sides as defined by the opening manually or using an applicator device). The sides of the fixation component 104 as defined by the opening interlock to securely hold the linear element 40. The fixation component 104 or the contact component 101 may include an accessory fixation structure (e.g., a locking pin) to help secure the fixation device 100 after deformation.

Figure 20A:
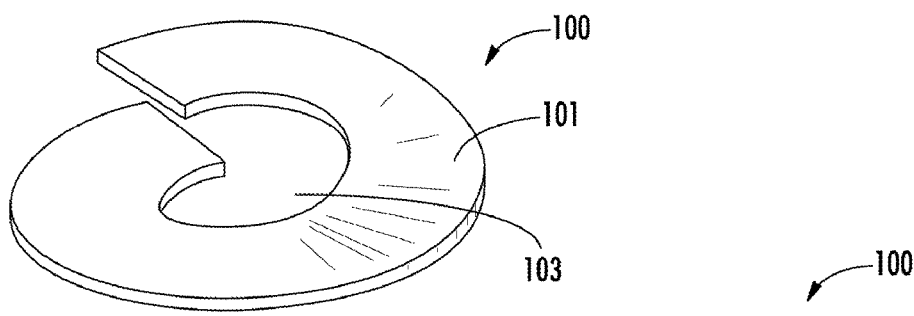
FIGS. 20A-20C depict another exemplary method of using another exemplary fixation device in accordance with the present invention.
Figure 20B:
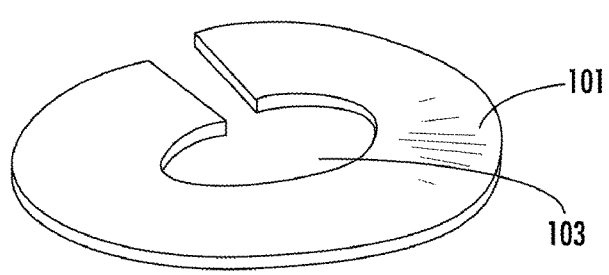
Figure 20C:
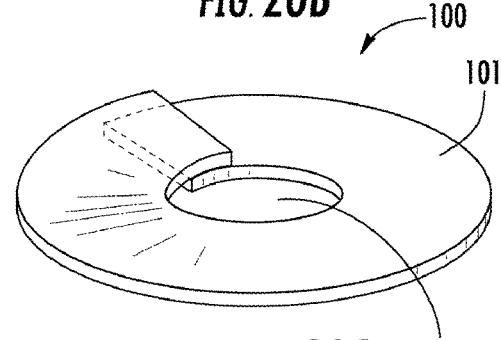

The fixation device can be configured with many different profiles to fit specific functions. In addition, the device can be deformed from a manufactured state (rest state), to a "pre-tensioned" deployment state, that upon transition of different sections becomes interlocking, for example transitioning from a spiral to a disc-like configuration. FIGS. 20A-20C depict an exemplary fixation device 100 that transitions from a spiral to a disc-like configuration. Either the central section or the lateral section can demonstrate components that interface or interlock to assist in device function, maintenance of the security of the linear element, of removal.

FIGS. 19A-19D depict exemplary fixation devices 100 and interlocking features. As depicted in FIG. 19A, the contact components 101 and 105, transition zones 111, fixation components 104 and 108, and medial joint 109 all include interlocking elements. FIGS. 19B and 19C depict close-up views of exemplary interlocking elements that include curved surfaces, notches, and hooks that engage each other.

FIG. 19D depicts another exemplary fixation device 100 including interlocking elements as secured to a linear element 40. The fixation device's interlocking elements may be on the interior interlocking surfaces of the fixation device 100 and/or may have exterior contours that match the exterior surface of the fixation device 100. FIG. 19E depicts an exemplary interlocking element including a latch or pin that engages a slot or hook. FIG. 19F depicts another exemplary interlocking element including a latch or pin that engages a slot or hook.

Exemplary fixation devices can include specific curves, notches, grooves, pins, slots, waves or other surface features within the receiving channel, slot, or groove to assist in secure fixation of the contained linear element at deployment.

FIGS. 20A-20C depict an exemplary embodiment of a fixation device 100 in accordance with the present invention. The fixation device's opening 103 has been depicted as a relatively large opening as compared to the outer circumference of the fixation device 100 to facilitate the demonstration of the function of the fixation device 100. Typically, the opening 103 has a much smaller circumference as compared to the outer circumference of the fixation device 100.

The fixation device 100 can be manufactured such that the lateral section (i.e., the contact component) is non-planar in a state of rest (natural state) as in FIG. 20A, with the spiral representing a greater than 360 degree rotation. In this embodiment, the edges of the lateral section that represent the borders of the common groove do not lie in the same horizontal plane at right angles to the axis of the device. Similarly the portions of the central section lie in different horizontal planes in relationship to the axis of the fixation device. Deployment of the device involves the application of a pre-deployment deforming ("pre-loading") force that increases the radius of the lateral section from a top view and flattens the lateral section such that the sides of the linear element-receiving groove are brought into similar planes in relationship to the longitudinal axis of the device as depicted in FIG. 20B. This pre-tensioning force imparts a stress within the body of the lateral section. A linear element is then positioned within the now visible common channel, and the deforming, pre-loading force is released such that the lateral sections and central sections are interlocked as in FIG. 20C. Because the imparted stress upon the lateral section is only partially released with device deployment, the stress provides an ongoing force approximating the central section and securing the linear element. Reversal of the deployment sequence removes the fixation device. Ridges, grooves, slots, or other features may be included to guide the movement from a natural "at rest" state to a pre-deployment (pre-tensioned) state or from the pre-deployment (pre-tensioned) state to a deployment state, or similarly to aid the reverse process (fixation device removal).

Figure 20D:
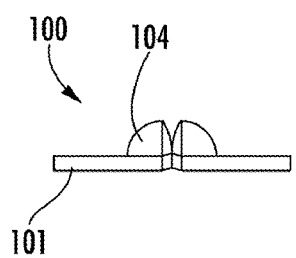
FIGS. 20D and 20E depict another exemplary method of using another exemplary fixation device in accordance with the present invention.
Figure 20E:
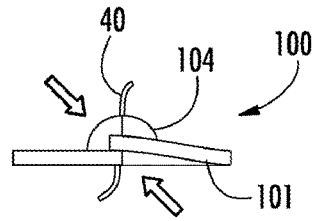

FIGS. 20D and 20E depict an exemplary fixation device 100 including a contact component 101 and fixation component 104 that function in the same manner as the fixation device depicted in FIGS. 20A-20C. In this regard, FIG. 20D depicts the exemplary fixation device 100 in a state corresponding to that of FIG. 20B. A linear element 40 is placed in the fixation device's opening which is visible in FIG. 20D. The pre-loading force is then released such that the fixation device 100 closes around the linear element 40 as in FIG. 20E.

Figure 21A:
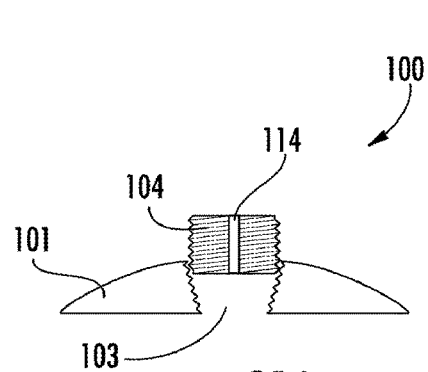
FIGS. 21A-21D depict another exemplary method of using another exemplary fixation device and another exemplary application device in accordance with the present invention.
Figure 21B:
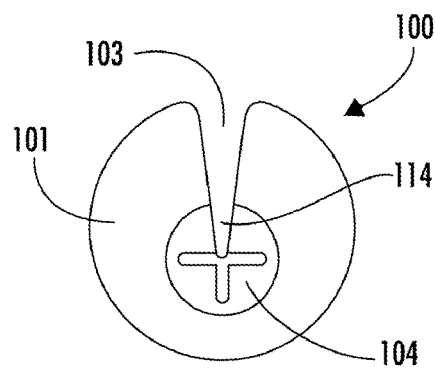

FIGS. 21A-21D depict an exemplary fixation device 100 and an exemplary applicator device 50. The fixation device 100 includes a contact component 101 having a contact surface 102 and an opening 103. The contact component 101 has tapered walls with receiving threads that define the opening 103. The fixation device 100 also includes a fixation component 104 (e.g., a hollow screw). The fixation component 104 includes a channel 114 and threads that engage the receiving threads of the contact component 101. As depicted in FIG. 21B, the contact component's tapered walls and the fixation component's channel 114 include a gap to facilitate placement of a linear element.

Figure 21C:
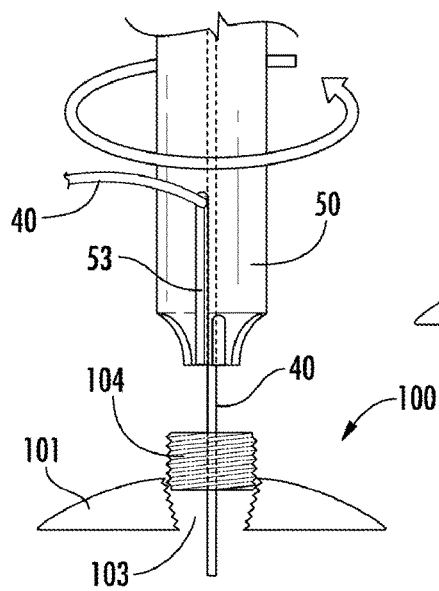
Figure 21D:
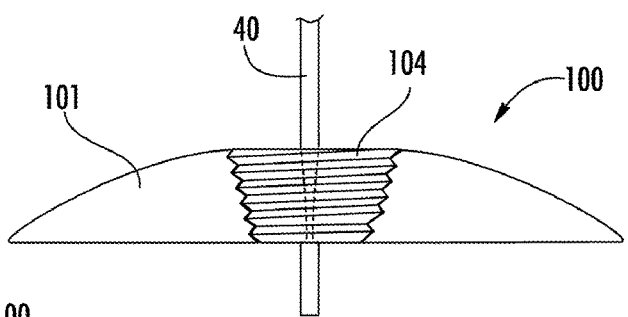

FIG. 21C depicts a linear element 40 loaded into the fixation device 100 and applicator device 50. The applicator device 50 includes a slot 53 (e.g., a slot, groove, notch, hole, channel, star-drive) to accommodate the linear element 40 without impinging, dividing, or damaging the linear element 40. The tip of the applicator device 50 engages the fixation component 104 (e.g., via a Phillips-head screw interface as depicted). When a rotational force is applied to the applicator device 50, the fixation component 104 is threaded more deeply into the contact component 101. Typically, at least the lower portion of the fixation component 104 is a slightly deformable material. As the fixation component 104 is driven into the contact component 101, at least the lower portion of the fixation component 104 deforms to close around the linear element 40 (i.e., the channel 114 shrink as the fixation component 104 is compressed).

The fixation component 104 can be in two or more portions or can exhibit slots or grooves such that the channel 114 is more efficiently compressed (advanced centrally) as rotational motion is imparted. The fixation component 104 can also be connected to the contact component 101 with deformable transition zone elements that can twist and reduce the diameter of the common channel, slot, or groove. The fixation component 104 may exhibit posts, tabs, or other features that interlock with the contact component 101 when the fixation component 104 is rotated in relationship to the contact component 101. In each of these embodiments, reversal of the rotational force releases the fixed linear element.

Figure 22A:
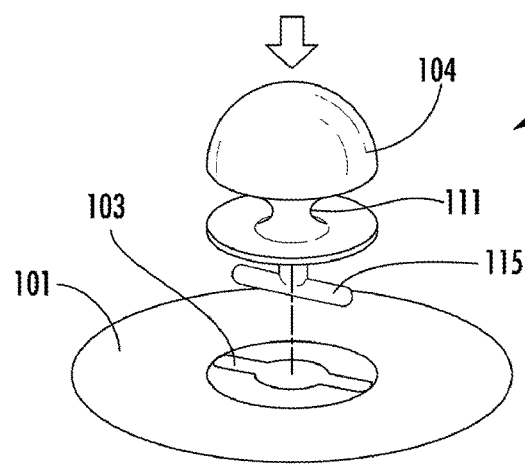
FIG. 22A depicts another exemplary fixation device in accordance with the present invention.
Figure 22B:
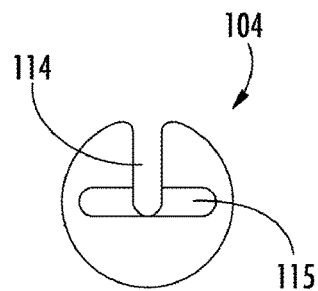
FIG. 22B depicts an exemplary fixation component of an exemplary fixation device in accordance with the present invention.
Figure 22C:
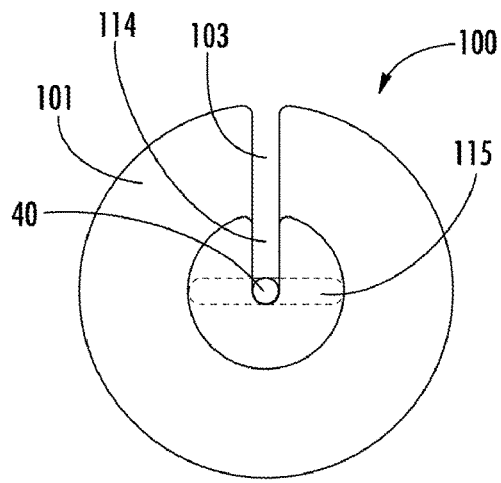
FIGS. 22C and 22D depict another exemplary method of using another exemplary fixation device and another exemplary application device in accordance with the present invention.

FIGS. 22A-22D depict exemplary fixation devices 100 including contact components 101 and fixation components 104. The contact components 101 have an opening 103. The fixation components 104 each include a channel 114 and a T-shaped post 115, and the openings 103 are shaped to receive the T-shaped post 115 at only particular orientations. The contact component's opening 103 in FIGS. 22C and 22D also extends to the outer edge of the contact component 101. FIG. 22B depicts a bottom view of the fixation components 104.

Figure 22D:
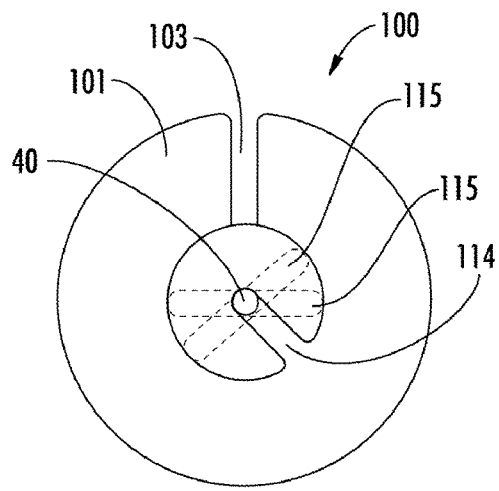

A linear element may be passed through the opening 103 and into the channel 114. As depicted in FIG. 22A, the fixation component 104 and its T-shaped post 115 are aligned with and inserted into the opening 103. The fixation component 104 may be rotated within the contact component 101 to align the opening 103 and channel 114 as depicted in the overhead view of FIG. 22C. A linear element 40 may then be provided in the opening 103 and channel 114. The fixation component 104 is rotated within the contact component 101 to secure the linear element 40 as depicted in FIG. 22D. The contact component 101 and fixation component 104 may be provided with additional features, such as ramps, tabs, and/or posts, that interact with the T-shaped post 115 to increase the force applied to the linear element when the fixation component 104 is rotated within the contact component 101.

FIGS. 23A-23D depict an exemplary fixation device and an exemplary applicator device 50 in accordance with the present invention. The fixation device 100 includes a contact component 101, a fixation component 104, and a transition zone 111. The surface contours of both the transition zone 111 and the fixation component 104 can facilitate both deployment of the fixation device 100 and removal of the fixation device 100. In this embodiment, the transition zone 111 has two parallel flat surfaces on opposite sides as shown by the dotted lines in FIG. 23A. The fixation component 104 has a hexagonal shape as seen from the top view. Separation of the fixation component 104 from the contact component 101 can be accomplished by turning or twisting the fixation component 104 around an axis defined by a common channel 114 (e.g., a slot or groove) of the fixation device 100. The flat surfaces of the fixation device 100 interact with an applicator device 50 that may also serve as a removal tool.

Although hexagonal shapes and parallel surfaces have been described, other shape variations are within the scope of the present invention. For example, the fixation component 104 may include two parallel flat surfaces rather than a hexagonal shape. The contact component 101 may also include similar contour features such as flat surfaces, holes, slots, grooves, or notches to help facilitate removal. In addition, a common slot or groove in the lateral section can function as a point of stabilization with a removal tool.

Any two of the three sections (i.e., the contact component 101, the transition zone 111, and/or the fixation component 104) can be engaged to separate the fixation component 104 from the contact component 101 in this manner. For example, the applicator device 50 may engage the contact component 101 and the transition zone 111, the contact component 101 and the fixation component 104, or the transition zone 111 and the fixation component 104 for this purpose.

\* \* \*

Exemplary Embodiments

[1]. A fixation device for securing a linear element extending through a perforation in a work-piece, said fixation device comprising:

a. a base section having a contact surface on one end shaped to engage a work-piece;

b. an apical (central) section opposite the contact surface of the base section; and c. a groove, slot, channel, or receiving contour so shaped as to accommodate a linear element, said groove, slot, channel, or receiving contour extending at a minimum through the base section and into the apical section;

d. said groove, slot, channel, or receiving contour at a pre-deployment rest state defining the longitudinal axis of the fixation device;

said fixation device being so constructed as to be deformable such that said deformation will constrict the space within said groove, slot, channel, or receiving contour thereby securing a linear element which is positioned within said groove, slot, channel, or receiving contour at the time of deformational deployment;

so constructed such that a force vector applied a linear element thus secured will engage the fixation device to the work-piece when said linear element extends through a work-piece and the force vector is in the direction of said work-piece.

[2]. A fixation device for securing a linear element extending through a perforation in a work-piece, said fixation device comprising:

a. a base section having a contact surface on one end shaped to engage a work-piece after deformation of said fixation device, said based section having a non-planar orientation at rest state with overlapping surfaces in relationship to the longitudinal axis of the device;

b. an apical section opposite the contact surface of the contact section; and c. a groove, slot, channel, or receiving contour so shaped as to accommodate a linear element after partial deformation of said device; said groove, slot, channel, or receiving contour extending through both base section and apical section at such time as the device is partially deformed;

d. said groove, slot, channel, or receiving contour at said partially deformed state defining the longitudinal axis of the fixation device;

said fixation device being so constructed that with completion of deformation said overlapping surfaces can be transposed in relationship to the longitudinal axis of said fixation device such that said deformation and transposition secure a linear element which is positioned within the groove, slot, channel, or receiving contour of the fixation device at the time of partial deformation;

so constructed such that a force vector applied a linear element thus secured will engage the fixation device to the work-piece when said linear element extends through a work-piece and the force vector is in the direction of said work-piece.

[3]. A fixation device for securing a linear element extending through a perforation in a work-piece, said fixation device comprising:

a. a base section having a contact surface on one end shaped to engage a work-piece;

b. an apical section opposite the contact surface of the contact section, said apical section exhibiting a non-planar orientation at rest state with overlapping surfaces in relationship to the longitudinal axis of the device; and c. a groove, slot, channel, or receiving contour so shaped as to accommodate a linear element after partial deformation of said device; said groove, slot, channel, or receiving contour extending through both base section and apical section at such time as the device is partially deformed;

d. said groove, slot, channel, or receiving contour at said partially deformed state defining the longitudinal axis of the fixation device;

said fixation device being so constructed that with completion of deformation said overlapping surfaces can be transposed in relationship to the longitudinal axis of said fixation device such that said deformation and transposition secure a linear element which is positioned within the groove, slot, channel, or receiving contour of the fixation device at the time of partial deformation;

so constructed such that a force vector applied a linear element thus secured will engage the fixation device to the work-piece when said linear element extends through a work-piece and the force vector is in the direction of said work-piece.

[4]. A double fixation device exhibiting two fixation devices as in (1), (2), or (3) wherein;

a. said individual fixation devices are connected at the apical terminus of each device such that the grooves, slots, channels, or receiving contours so shaped as to accommodate a linear element within each individual fixation device are aligned to create a common groove, slot, channel, or receiving contour along the entirety of said double fixation device; and b. each individual fixation device is separately deployable, either simultaneously or in series, while a common linear element is positioned within the common groove, slot, channel, or receiving contour;

c. with said connection between individual fixation devices being divisible so as to create two independently functioning fixation devices after deformational deployment and separation.

[5]. A fixation device as in [1-4] constructed of a malleable material such that the deploying deformation may be induced by means of a mechanical force applied to the fixation device.

[6]. A fixation device as in [1-4] constructed of a material such that deformation may be facilitated by the application of heat, ultrasound, or other energy source.

[7]. A fixation device as in [1-4] wherein deformation is accomplished by means of bending or folding.

[8]. A fixation device as in [1] or [4] wherein the apical segments can be folded into a channel within the base segment.

[9]. A fixation device as in [1-4] where the device exhibits interactive pins, slots, tabs, grooves, notches, or other surface contour features which can interact to stabilize the deployment state.

[10]. A fixation device as in [1-4] which exhibits an adhesive layer on at least one surface of the device.

[11]. A fixation device as in [1-4] which exhibits a transition zone between a base section and an apical section, and a. separation of the base section and apical section at said transition zone can be accomplished by cutting, compressing, distorting, twisting, heating, breaking, or other means; and b. said separation of base and apical sections releasing the constriction of the groove, slot, channel, or receiving contour which secures the contained linear element allowing separation of the linear element from the deployed fixation device.

[12]. A fixation device as in [1-4] wherein the apical section or a transition zone between the apical section and base section can be deformed by means of a malleable clip which remains attached to the fixation device during deployment.

[13]. A fixation device as in [1-4] with a secondary surface groove, slot, channel, notch, or other surface contour which allows access to the secured linear device within said fixation device after deployment.

[14]. A device as in [1-4] that exhibits ridges, grooves, shelves, threads, adhesive layer or other surface features within the common channel to assist in securing of a linear element.

[15]. A device as in [1-4] that exhibits slots, grooves, holes, bevels, flattened surfaces, or other surface characteristics to assist in device deployment or removal.

[16]. A device as in [1-4] wherein the fixation section exhibits tabs, wings, flanges, or other surface features which can be used to secondarily adjust or to release a contained linear element.

[17]. A device as in [1] and [2] wherein the base plate or fixation section exhibit holes, perforations, channels or other surface features.

[18]. A device as in [1-4] wherein the base plate and/or fixation section exhibits holes, perforations, channels or other surface features; and a. said holes, perforations, channels or other surface features can be utilized to fix the base section to a work-piece;

b. said fixation of the base section to a work-piece being accomplished by various means including adhesion, suturing, sewing, pins, screws, or other mechanisms, such that c. once deployed to secure a linear element and fixed to the work-piece through which said linear element emerges, said linear element is secured to force vectors both toward the work-piece and away from the work-piece.

[19]. A device as in [1-4] that exhibits color variation.

[20]. A storage container for devices as in [1-4], said storage container exhibiting slots, grooves, notches or other surface features so configured as to hold said devices in orientation for loading onto an applicator.

[21]. An applicator for a device as in [1-4], said applicator allowing individual loading and deployment of said fixation device.

[22]. An applicator for a device as in [1-4], said applicator allowing loading and deployment of multiple said fixation devices.

[23]. An applicator for a device as in [1-4], said applicator exhibiting waves, grooves, or other surface features along the section where the fixation device is loaded into said applicator, with said waves, grooves, or other surface features producing a non-uniform deformation of the fixation device.

[24]. An applicator for a device as in [1-4], said applicator simultaneously exhibiting both a compressive surface and a cutting surface.

[25]. An applicator for a device as in [1-4], said applicator exhibiting bidirectional compressive surfaces and/or cutting surfaces.

[26]. An applicator for a device as in [1] and [2].

[27]. A device as in [1] and [2] wherein the device is symmetrical when rotated about an axis defined by the center of the common channel.

[28]. A device as in [1] and [2] wherein the base plate has a non-uniform radius when rotated about an axis defined by the center of the common channel.

[29]. A device as in [1] and [2] wherein the central fixation section has a non-symmetrical radius when rotated about an axis defined by the center of the common channel.

[30]. A device as in [1] and [2] wherein the device exhibits a slot or groove which extends from a lateral surface of a base plate to the common channel.

[31]. A device as in [1] and [2] wherein the device exhibits a slot or groove which extends from a side of a central fixation section to the common channel.

* * *

Exemplary Embodiments

[1]. A device comprising a base plate which exhibits an essentially flat surface on one side;
said base plate connected to a central fixation section on a side of the base plate opposite to said essentially flat surface;
said combined base plate and central fixation section containing a common channel or pathway which allows the positioning of a linear element through both base plate and central fixation section;
wherein the central fixation section can be purposefully deformed, such deformation causing a subsequent change in configuration of the common channel.

[2]. A device comprising two base plates, each of which exhibits an essentially flat surface on one side;
said base plates each connected to a central fixation segment on a side of the base plate opposite to the flat surface;
with said central fixation sections connected at the portion of the central fixation section opposite to the essentially flat surfaces of the base plates;
said base plates and central fixation sections containing a common channel or pathway which allows the positioning of a linear element through both base plates and both central fixation sections;
wherein both central fixation sections can be purposefully deformed, such deformation causing a subsequent change in configuration of the common channel.

[3]. A device as in [1] and [2] wherein the device is symmetrical when rotated about an axis defined by the center of the common channel.

[4]. A device as in [1] and [2] wherein the base plate has a non-uniform radius when rotated about an axis defined by the center of the common channel.

[5]. A device as in [1] and [2] wherein the central fixation section has a non-symmetrical radius when rotated about an axis defined by the center of the common channel.

[6]. A device as in [1] and [2] wherein a central fixation section exhibits a narrowing near the junction of said central fixation section with the base plate to which it is directly connected.

[7]. A device as in [1] and [2] wherein a central fixation section exhibits a narrowing near the terminus of the central section not connected directly to a base plate.

[8]. A device as in [1] and [2] wherein the device exhibits a slot or groove which extends from a lateral surface of a base plate to the common channel.

[9]. A device as in [1] and [2] wherein the device exhibits a slot or groove which extends from a side of a central fixation section to the common channel.

[10]. A device as in [1] and [2] that exhibits an adhesive layer applied to the common channel.

[11]. A device as in [1] and [2] that exhibits ridges, grooves, shelves, threads, or other textural features within the common channel.

[12]. A device as in [1] and [2] that exhibits color variations to assist in orientation or removal.

[13]. A device as in [1] and [2] that exhibits slots, grooves, holes, bevels, flattened surfaces, or other surface characteristics to assist in device placement or removal.

[14]. A device as in [1] and [2] wherein the fixation channel can be deformed by the application of a compressive force.

[15]. A device as in [1] and [2] wherein the fixation channel can be deformed by the controlled application of heat.

[16]. A device as in [1] and [2] wherein the fixation section exhibits tabs, wings, flanges, or other surface features which can be used to secondarily modify the fixation section in order to release a contained linear element.

[17]. A device as in [1] and [2] wherein once a deformed central section and the connected base plate can be separated by cutting, compressing, distorting, twisting, melting, breaking, or other means.

[18]. A device as in [1] and [2] wherein the base plate or fixation section exhibit holes or perforations.

[19]. A device as in [2] that exhibits a color difference between opposite fixation sections or base plates.

[20]. A device as in [2] that exhibits asymmetry along the longitudinal axis.

[21]. An applicator for a device as in [1] and [2], said applicator so shaped as to deform the fixation section in a uniform manner.

[22]. An applicator for a device as in [1] and [2], said applicator so shaped as to deform the fixation section in a non-uniform manner.

[23]. An applicator for a device as in [1] and [2], said applicator exhibiting a cutting surface so positioned as to align with the terminus of a fixation section opposite to the essentially flat surface of a base plate.

[24]. An applicator for a device as in [1] and [2], said applicator simultaneously exhibiting both a compressive surface and a cutting surface.

[25]. An applicator for a device as in [1] and [2].

[26]. A storage container for devices as in [1] and [2], said storage container exhibiting slots, grooves, notches or other surface features so configured as to hold said devices in orientation for loading onto an applicator.

[27]. A multi-load applicator capable of holding two or more devices as in [1] and/or [2] such that said common channels or pathways of said devices are parallel.

[28]. A multi-load applicator capable of holding two or more devices as in [1] and/or [2] such that said common channels or pathways of said devices are aligned along a single axis.

* * *

To supplement the present disclosure, this application incorporates entirely by reference the following commonly assigned patent application publications, and patent applications: International Patent Application Publication No. WO 2012/135735 for a Force Modulating Tissue Bridge (Eaves); U.S. Patent Application No. 61/469,966 for a Pre-Tensioned/Pre-Stressed Device, filed Mar. 31, 2011 (Eaves); U.S. Patent Application No. 61/470,158 for a Device and Method for Applying a Pre-Tensioned Element to Opposing Surfaces, filed Mar. 31, 2011 (Eaves); International Patent Application Publication No. WO 2013/059600 for a Removable Covering and Interactive Packaging (Eaves); U.S. Patent Application No. 61/654,748 for a Removable Covering and Interactive Packaging, filed Jun. 1, 2012 (Eaves); U.S. Patent Application No. 61/549,317 for a Protective Covering for Adhesive Backed Articles and Methods of Applying the Same, filed Oct. 20, 2011 (Eaves); and U.S. Patent Application No. 61/561,522 for a Protective Packaging for Adhesive Backed Articles, filed Nov. 18, 2011 (Eaves).

* * *

In the specification and/or figures, typical embodiments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. A fixation device for securing a linear element to a workpiece, comprising:
a first contact component having (i) a first contact surface for application to a workpiece and (ii) a first opening for receiving a linear element;
a first fixation component for securing a portion of the linear element on a side of said first contact component opposite said first contact surface;
a second contact component having (i) a second contact surface for application to a workpiece and (ii) a second opening for receiving a linear element; and
a second fixation component for securing a portion of the linear element on a side of said second contact component opposite said second contact surface;
wherein said first fixation component engages said first contact component to prevent passage of the linear element's secured portion through the workpiece when a tension is applied to the linear element in a direction opposite said first contact surface;
wherein said second fixation component engages said second contact component to prevent passage of the linear element's secured portion through the workpiece when a tension is applied to the linear element in a direction opposite said second contact surface; and
wherein said first fixation component and said second fixation component are positioned between said first contact component and said second contact component.

2. The fixation device according to claim 1, wherein, said first contact component and said first fixation component are physically connected.

3. The fixation device according to claim 1, wherein, as measured in a plane parallel to the first contact surface, the fixation device's cross sectional area at the area of engagement between the first contact component and the first fixation component is smaller than (i) the first contact component's average cross sectional area and (ii) the first fixation component's average cross sectional area.

4. The fixation device according to claim 1, wherein the exterior surface of the fixation device opposite the first contact surface comprises an arcuate surface.

5. The fixation device according to claim 1, wherein the ratio of (i) the height of the fixation device as measured from the first contact surface to the end of the first fixation component opposite the first contact surface to (ii) the maximum width of the first contact surface is approximately one or less.

6. The fixation device according to claim 1, wherein said first contact component's opening comprises a hole.

7. The fixation device according to claim 1, wherein said first contact component's opening comprises a groove.

8. The fixation device according to claim 1, wherein said first contact component's opening comprises a channel.

9. The fixation device according to claim 1, wherein said first fixation component comprises an adhesive.

10. The fixation device according to claim 1, wherein said first fixation component comprises a jagged surface for engaging the linear element.

11. The fixation device according to claim 1, wherein the fixation device comprises polymeric material.

12. The fixation device according to claim 1, wherein said first contact component's contact surface comprises an adhesive, medication, and/or padding.

13. The fixation device according to claim 2, wherein:
said second fixation component is physically connected to said second contact component; and
the fixation device comprises a medial joint that physically connects said first fixation component and said second fixation to one another so that said first fixation component and said second fixation component are positioned between said first contact component and said second contact component.

14. A fixation device for securing a linear element to a workpiece, comprising:
a first contact component having (i) a first contact surface for application to a workpiece and (ii) a first opening for receiving a linear element;
a first fixation component for securing a portion of the linear element on a side of said first contact component opposite said first contact surface;
a second contact component having (i) a second contact surface for application to a workpiece and (ii) a second opening for receiving a linear element; and
a second fixation component for securing a portion of the linear element on a side of said second contact component opposite said second contact surface;
wherein said first fixation component engages said first contact component to prevent passage of the linear element's secured portion through the workpiece when a tension is applied to the linear element in a direction opposite said first contact surface;
wherein said second fixation component engages said second contact component to prevent passage of the linear element's secured portion through the workpiece when a tension is applied to the linear element in a direction opposite said second contact surface;
wherein said first fixation component and said second fixation component are positioned between said first contact component and said second contact component; and
wherein said second contact component and said second fixation component are physically connected.

15. The fixation device according to claim 14, wherein, said first contact component and said first fixation component are physically connected.

16. The fixation device according to claim 14, wherein, as measured in a plane parallel to the second contact surface, the fixation device's cross sectional area at the area of engagement between the second contact component and the second fixation component is smaller than (i) the second contact component's average cross sectional area and (ii) the second fixation component's average cross sectional area.

17. The fixation device according to claim 14, wherein the exterior surface of the fixation device opposite the second contact surface comprises an arcuate surface.

18. The fixation device according to claim 14, wherein the ratio of (i) the height of the fixation device as measured from the second contact surface to the end of the second fixation component opposite the second contact surface to (ii) the maximum width of the second contact surface is approximately one or less.

19. The fixation device according to claim 14, wherein said second contact component's opening comprises a hole.

20. The fixation device according to claim 14, wherein said second contact component's opening comprises a groove.

21. The fixation device according to claim 14, wherein said second contact component's opening comprises a channel.

22. The fixation device according to claim 14, wherein said second fixation component comprises an adhesive.

23. The fixation device according to claim 14, wherein said second fixation component comprises a jagged surface for engaging the linear element.

24. The fixation device according to claim 14, wherein the fixation device comprises polymeric material.

25. The fixation device according to claim 14, wherein said second contact component's contact surface comprises an adhesive, medication, and/or padding.

26. The fixation device according to claim 15, comprising a medial joint that physically connects said first fixation component and said second fixation to one another so that said first fixation component and said second fixation component are positioned between said first contact component and said second contact component.

27. A fixation device for securing a linear element to a workpiece, comprising:
a first contact component having (i) a first contact surface for application to a workpiece and (ii) a first opening for receiving a linear element;
a first fixation component physically connected to said first contact component and arranged for securing a portion of the linear element on a side of said first contact component opposite said first contact surface;
a second contact component having (i) a second contact surface for application to a workpiece and (ii) a second opening for receiving a linear element; and
a second fixation component physically connected to said second contact component and arranged for securing a portion of the linear element on a side of said second contact component opposite said second contact surface,
wherein said first fixation component and said second fixation component are physically connected to one another so that said first fixation component and said second fixation component are positioned between said first contact component and said second contact component.

28. The fixation device according to claim 27, wherein, as measured in a plane parallel to the first contact surface, the fixation device's cross sectional area at the area of engagement between the first contact component and the first fixation component is smaller than (i) the first contact component's average cross sectional area and (ii) the first fixation component's average cross sectional area.

29. The fixation device according to claim 27, wherein the exterior surface of the fixation device opposite the first contact surface comprises an arcuate surface.

30. The fixation device according to claim 27, wherein the ratio of (i) the height of the fixation device as measured from the first contact surface to the end of the first fixation component opposite the first contact surface to (ii) the maximum width of the first contact surface is approximately one or less.

31. The fixation device according to claim 27, wherein said first contact component's opening comprises a hole.

32. The fixation device according to claim 27, wherein said first contact component's opening comprises a groove.

33. The fixation device according to claim 27, wherein said first contact component's opening comprises a channel.

34. The fixation device according to claim 27, wherein said first fixation component comprises an adhesive.

35. The fixation device according to claim 27, wherein said first fixation component comprises a jagged surface for engaging the linear element.

36. The fixation device according to claim 27, wherein the fixation device comprises polymeric material.

37. The fixation device according to claim 27, wherein said first contact component's contact surface comprises an adhesive, medication, and/or padding.

38. The fixation device according to claim 27, comprising a medial joint that physically connects said first fixation component and said second fixation to one another so that said first fixation component and said second fixation component are positioned between said first contact component and said second contact component.

* * * * *

UNITED STATES PATENT AND TRADEMARK OFFICE
CERTIFICATE OF CORRECTION

PATENT NO. : 10,094,401 B2
APPLICATION NO. : 14/706572
DATED : October 9, 2018
INVENTOR(S) : Felmont F. Eaves, III Page 1 of 1

It is certified that error appears in the above-identified patent and that said Letters Patent is hereby corrected as shown below:

In the Claims

Column 24, Claim 13, Line 31, delete "fixation to" and replace with -- fixation component to --

Column 25, Claim 26, Line 37, delete "fixation to" and replace with -- fixation component to --

Column 26, Claim 38, Line 46, delete "fixation to" and replace with -- fixation component to --

Signed and Sealed this
Seventh Day of April, 2020

Andrei Iancu
*Director of the United States Patent and Trademark Office*